United States Patent
Zadini et al.

(10) Patent No.: US 6,747,184 B2
(45) Date of Patent: *Jun. 8, 2004

(54) CATAMENIAL DEVICE FOR BLOOD LEAKAGE PREVENTION

(76) Inventors: Filiberto Zadini, 2237 Hilltop Ln., Camarillo, CA (US) 93012; Giorgio Zadini, 2237 Hilltop Ln., Camarillo, CA (US) 93012

( * ) Notice: Subject to any disclaimer, the term of this patent is extended or adjusted under 35 U.S.C. 154(b) by 0 days.

This patent is subject to a terminal disclaimer.

(21) Appl. No.: 10/410,743

(22) Filed: Apr. 10, 2003

(65) Prior Publication Data

US 2003/0199840 A1 Oct. 23, 2003

Related U.S. Application Data

(63) Continuation-in-part of application No. 10/142,597, filed on May 9, 2002, now Pat. No. 6,570,052, which is a continuation-in-part of application No. 09/861,332, filed on May 17, 2001, now Pat. No. 6,559,352, which is a continuation-in-part of application No. 09/372,861, filed on Aug. 12, 1999, now Pat. No. 6,540,728, which is a continuation-in-part of application No. 08/907,529, filed on Aug. 8, 1997, now Pat. No. 5,947,992, which is a continuation-in-part of application No. 08/391,342, filed on Feb. 21, 1995, now Pat. No. 5,674,239.

(51) Int. Cl.$^7$ ............................................. A61F 13/15
(52) U.S. Cl. ...................................... 604/358; 604/330
(58) Field of Search ........................... 604/1–3, 11–18, 604/96.01, 99.01, 317, 322, 330, 331, 358, 367, 369, 374, 385.1, 385.12, 385.17, 385.18, 540, 904; 606/1, 119, 191–193, 196; 128/836

(56) References Cited

U.S. PATENT DOCUMENTS

| | | | | |
|---|---|---|---|---|
| 5,609,586 A | * | 3/1997 | Zadini et al. | 604/358 |
| 5,674,239 A | * | 10/1997 | Zadini et al. | 606/193 |
| 5,772,645 A | * | 6/1998 | Zadini et al. | 604/358 |
| 6,570,052 B2 | * | 5/2003 | Zadini et al. | 604/358 |

* cited by examiner

*Primary Examiner*—Brian L. Casler
*Assistant Examiner*—Michael M Thompson

(57) ABSTRACT

A catamenial device for blood leakage prevention composed of an inflatable-expandable member and an absorbent intravaginal member such as a tampon. The inflatable-expandable member houses a resiliently expandable inflation member generally made of open cell foam. Prior insertion into a vaginal canal, the inflation member is in a contracted state. Upon placement to proper vaginal location, the inflation member expands by resiliency drawing air from a space inside the balloon or a reservoir of the balloon where the air has been displaced and housed when the air has been squeezed out from the open cell foam when the inflation member has been compressed prior to insertion. Inflation-expansion of the inflatable member can be activated manually by the user or via an intravaginal applicator which has the dual function of inserting and delivering the device into the vagina and that of actuating the inflation-expansion of the inflatable member.

8 Claims, 25 Drawing Sheets

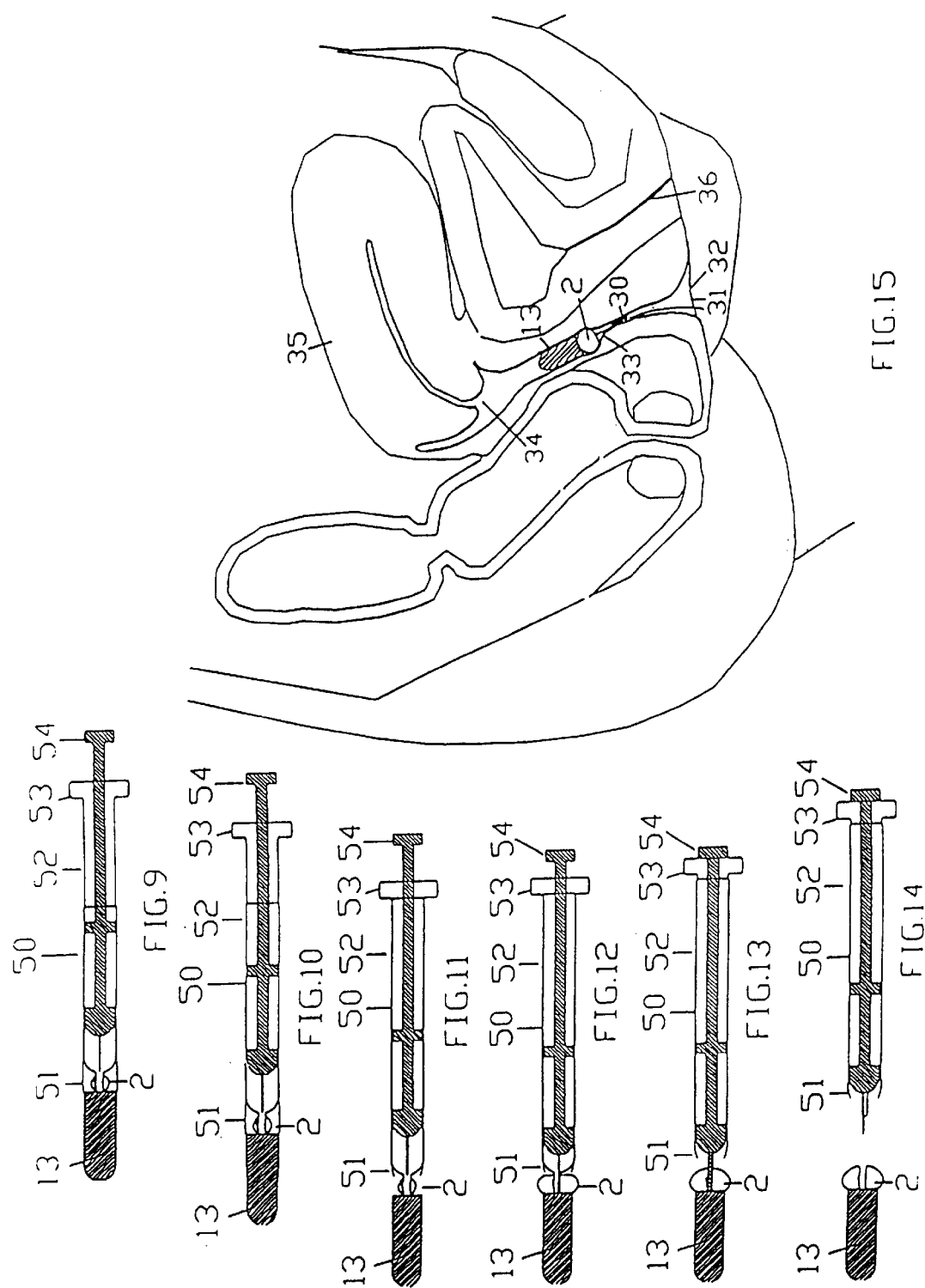

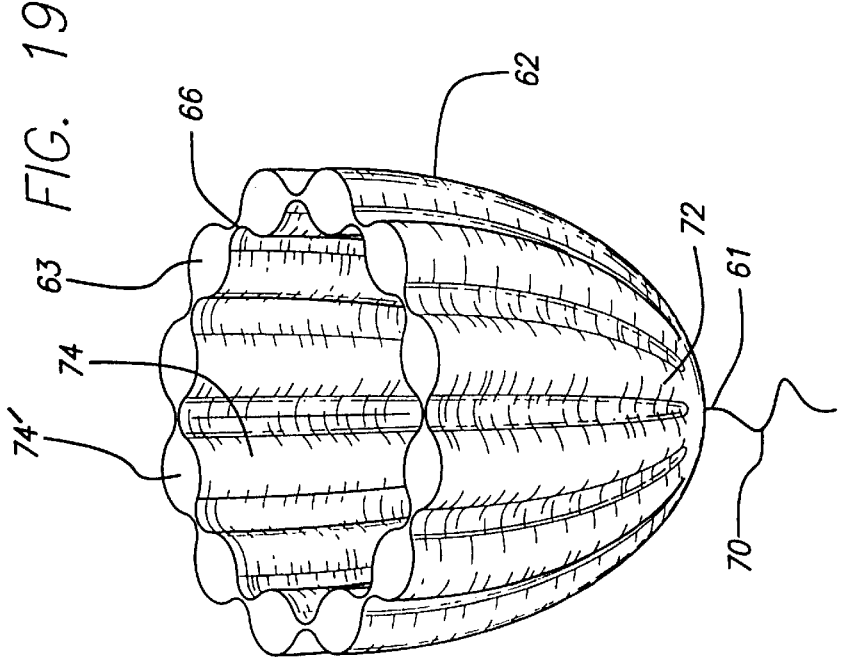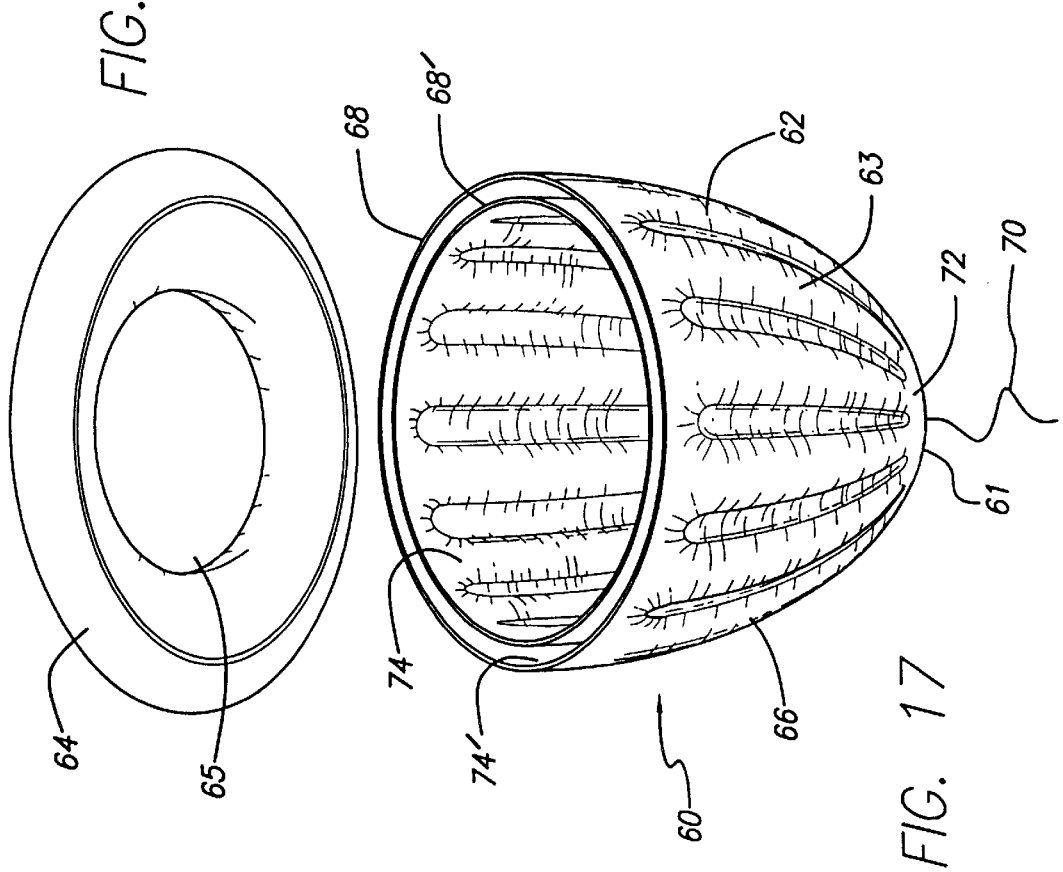

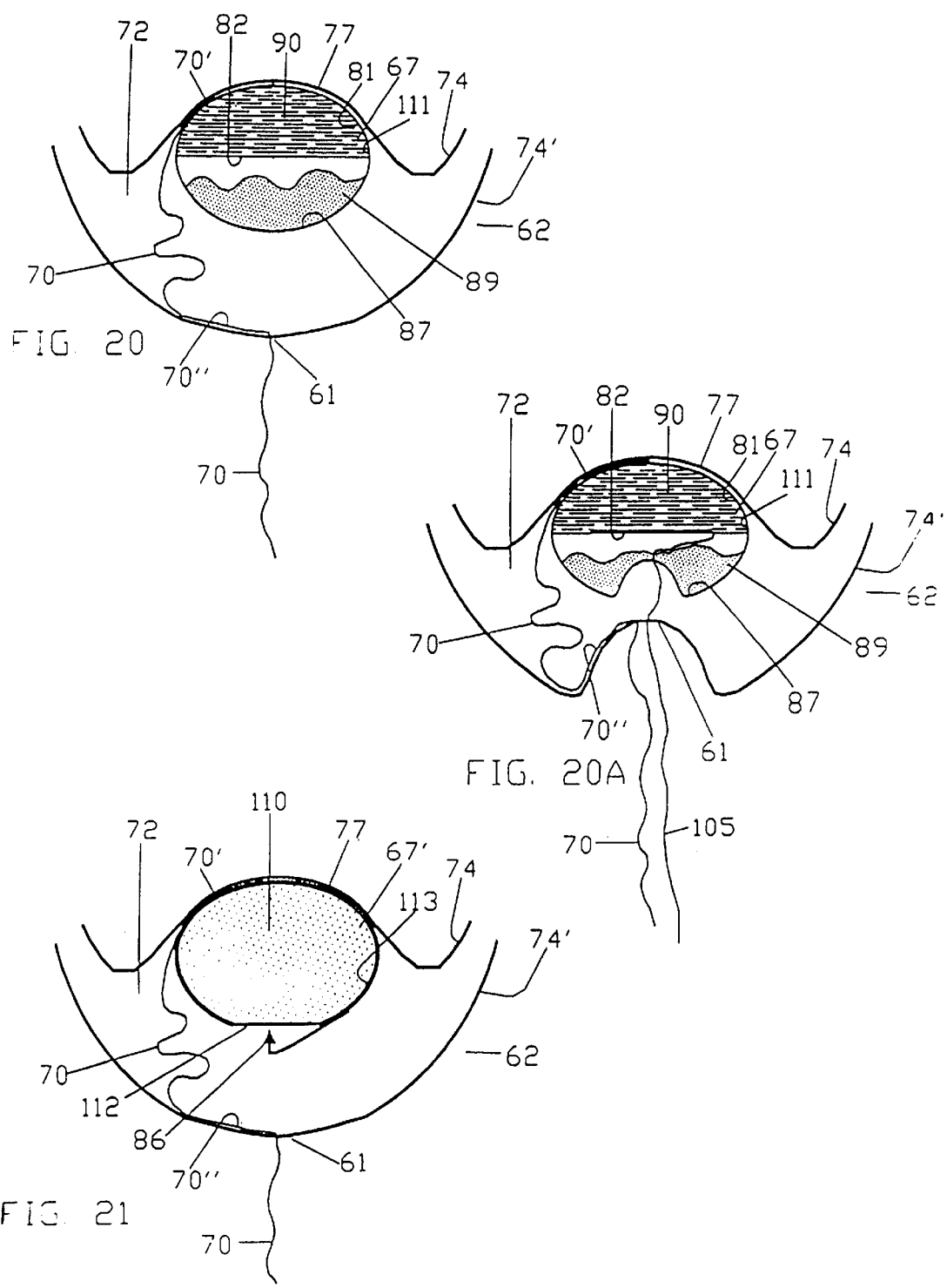

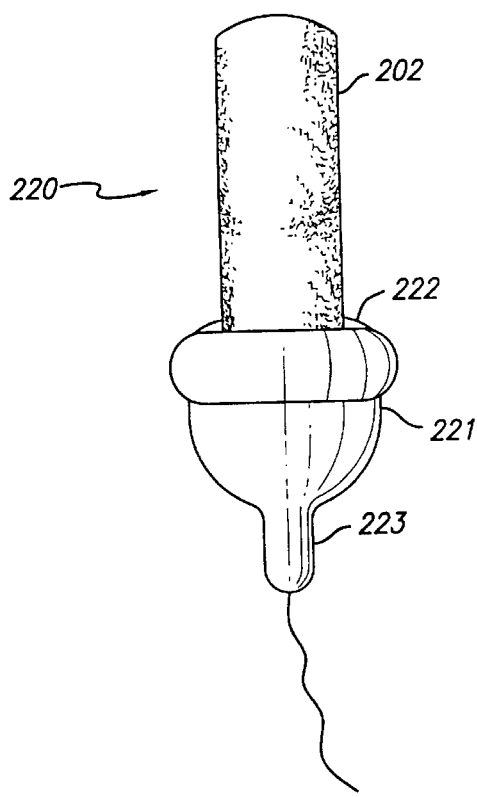
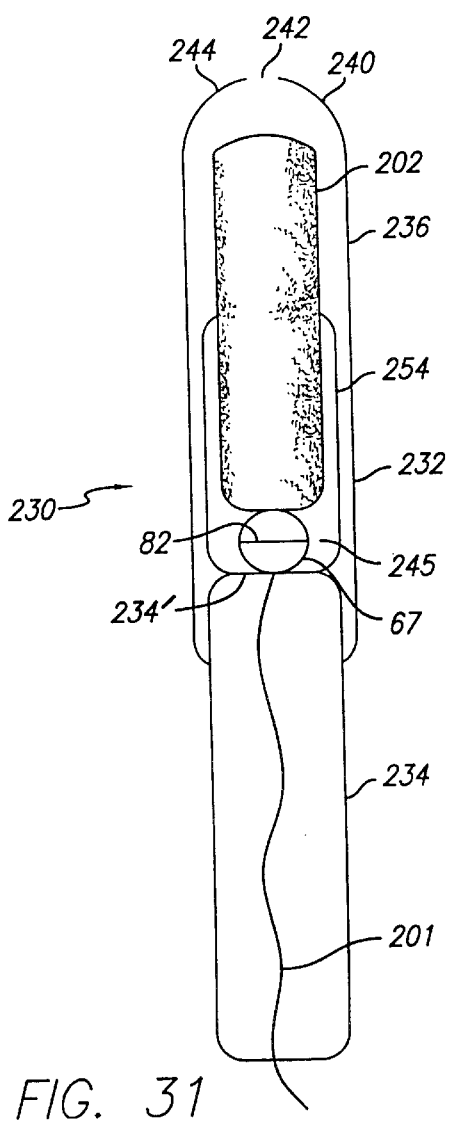
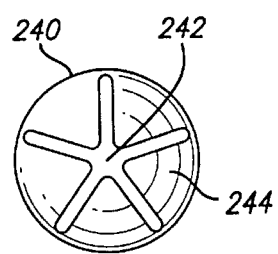
FIG. 30
FIG. 31A
FIG. 31

CATAMENIAL DEVICE FOR BLOOD LEAKAGE PREVENTION

RELATED CASES

This application is a Continuation in Part of our application Ser. No. 10/142,597 filed on May 9, 2002 now U.S. Pat. No. 6,570,052, which is a Continuation in Part of patent application Ser. No. 09/861,332 filed on May 17, 2001, now U.S. Pat. No. 6,559,352, which is a Continuation in Part of patent aplication Ser. No. 09/372,861 filed on Aug. 12, 1999, now issued as U.S. Pat. No. 6,540,728 on Apr. 1, 2003, which is a Continuation in Part of our application Ser. No. 08/907,529, filed on Aug. 8, 1997, issued as U.S. Pat. No. 5,947,992 on Sep. 7, 1999, which is a Continuation in Part of patent application Ser. No. 08/391,342 filed on Feb. 21, 1995, issued as U.S. Pat. No. 5,674,239 on Oct. 7, 1997.

FIELD OF THE INVENTION

This invention relates to obstetrical-gynecological devices, more specifically to intravaginal devices designed to collect menstrual blood and to prevent leaking or exit of blood or any other organic fluid from the vagina.

BACKGROUND

Description of the Prior Art

The vagina is a musculomembranous tubular organ extending from the uterine cervix to the exterior of the body. The vaginal canal is about 9 or 10 cm long. Its lumen is generally quite small, and the walls that surround it are usually in contact with each other. Various are the organic fluids which pass through the vaginal canal during the female lifetime, such as blood, vaginal secretion fluids, amniotic fluid, etc.

An important organic fluid passing through the vaginal canal and exiting through the vaginal orifice is blood, either as a result of physiological conditions such as the menstrual period or as a result of pathological conditions such as cervical or endometrial carcinoma. The various inconveniences to women resulting from the occurrence of physiological bleeding occurring during the menstrual period have prompted attempts to regulate or control the outflow of menstrual bleeding according to the women personal and social needs. For the purpose of controlling the outflow of menstrual blood, vaginal tampons were introduced a few decades ago. Vaginal tampons are common catamenial devices made of absorbing material and insertable into the vagina by the female user. Due to their absorbing material, tampons, once inserted into the vagina, begin to absorb upon contact the blood they meet, which outflows from the cervical canal into the vagina, and function as reservoirs aiming at delaying exit of the blood from the vaginal orifice conceivably until they become saturated with blood and, in so doing, they exert a regulatory effect on the outflow of menstrual bleeding to meet women's' needs or preferences.

However, regardless of their absorbency capabilities, tampons, for various reasons, are known to allow leakage of menstrual blood at rather unpredictable time or shortly after insertion, falling short of providing the regulatory effect which is the very reason for their use. No known tampon is capable of preventing leakage of blood from the vaginal orifice, regardless of shape, size, intravaginal resting site, absorbency capabilities of the material or materials of which they are made of, etc. Blood may leak from the vaginal orifice because the tampon is too early saturated with blood or because the blood flow is disproportionately heavy for the absorbency capabilities of the inserted tampon or because the tampon does not provide an adequate sealing with the vaginal walls or orifice or for all the above reasons variously combined.

Despite the use of tampons, therefore, leakage of blood from the vaginal orifice is almost the rule during the days of the vaginal bleeding and its occurrence may result in a great deal of annoyance and inconvenience to the woman: leakage indeed actually defeats the main purpose for which tampons are used.

Prior art deals with the problem of leakage of menstrual blood through the tampons, some inventions by providing additional blood reservoirs to the tampons, some others by increasing the tampons absorbing capabilities by the means of improved absorbing material, and others by using absorbing pads to apply in correspondence of the vaginal orifice to capture the blood escaped from the tampon. In all such cases, main object of the prior art is rather to minimize and possibly delay the outflow of blood, rather than reliably preventing the leakage of blood until it is the appropriate time for the woman, as determined by the woman rather than by her endometrium, to permit exit of the menstrual blood from the vaginal orifice.

No known catamenial device has been disclosed to provide means of preventing leakage of menstrual blood by entailing the use of an intravaginal balloon.

Another group of catamenial devices introduced for the purpose of avoiding leakage of menstrual blood are the menstrual cups. Indeed cup-shaped intravaginal devices for collection of menstrual blood are not new in the art of feminine hygiene. U.S. Pat. Nos. 3,845,766 by Zoller, 3,626, 942 by Waldron, 2,534,900 by Chalmers and 5,295,984 by Audrey all disclose a cup shaped menstrual collector made of flexible material impervious to fluid inserted into the vaginal canal for the purpose of collecting menstrual blood and preventing leakage of blood from the vaginal orifice. These devices all suffer from poor ergonomic design. They are all bulky, necessarily of large diameter, difficult to insert and remove. They all have a resilient circular rim that regardless of the material is made of is necessarily significantly larger than the diameter of the vaginal orifice they have to pass through during insertion and during removal. Regardless of the individual differences among the menstrual blood collector cups, the general design of all these devices makes their insertion into the vaginal canal an uncomfortable and difficult task. Removal of these devices is even more difficult and uncomfortable for the user than the insertion. Furthermore on their removal spillage of blood is a very frequent occurrence. Indeed none of the menstrual cups is provided with an effective simple sealable closure apparatus of the cup opening apt to prevent spillage of blood. A lot of expertise has to be learned by the user before effective insertion and removal of these devices can be achieved and no matter how expert the user can become, the use of the above mentioned menstrual cups is unavoidably associated with poor tolerance during use, discomfort on insertion and removal and in general difficult application.

Zadini et al disclose in their patent application Ser. No. 08/391,342 an inflatable device for sealable closure of the vaginal canal as a standing alone device and as a device associated with an intravaginal tampon. In FIG. 5 of the above cited Zadini's patent, an inflatable cup shaped member is described associated with a tampon. While this inflatable device offers advantages with respect to the priorly cited menstrual cups, being undeniably capable of being inserted into the vagina and removed from it in an easy and comfortable fashion being deflatable, still has the drawback of not being able to collect the blood escaped from tampon absorption and of allowing spillage of blood on removal as with all priorly cited menstrual cups.

BRIEF SUMMARY OF THE INVENTION

The present invention comprises an intravaginal inflatable cup shaped member capable of providing reliable vaginal closure to outflow of organic fluids such as menstrual blood from the vaginal orifice until the woman determines to be the appropriate time for allowing exit of the menstrual blood from the vaginal orifice, and also provides reliable vaginal closure to pathological bleeding. Vaginal closure is achieved by an inflatable member, impermeable to fluids, easily self-adaptable to the variability of size and shape of the vaginal lumen and to the variability of smoothness of the vaginal walls, said inflatable member expanding to exert a gentle pressure on the vaginal mucosa, such a pressure being sufficient to prevent passage of blood between the inflatable member itself and the vaginal mucosa. The inflatable cup shaped device is inserted into the vagina and extracted from it through the vaginal orifice in a deflated status allowing an easy and discomfort free insertion and extraction.

The device is provided with an automatic sealable closure of the opening of the cup to prevent spillage of blood on removal.

The device may be used, as a stand-alone intravaginal device, or may be used in combination with blood absorbing means such as tampons.

When used in cases of pathological vaginal bleeding, the inflatable intravaginal cup-shaped member, comprising material substantially impermeable to fluids, expands to exert pressure on the vaginal mucosa to prevent passage of blood between the inflatable device and the vaginal mucosa, such prevention of passage of blood resulting in a blockage to intravaginal transit of blood.

OBJECT OF THE INVENTION

It is an object of the present invention to propose a device that conceivably offers a solution to the problem of untimely leakage of menstrual blood. As such, i.e. if employed as a means for prevention of leakage of menstrual blood, one embodiment of the present invention could be used in combination with blood absorbing material, such as tampons.

However, it may also be used alone to provide means for prevention of blood leakage, or, for that same purpose, it may be used in combination with other devices or suitable components employed in association with menstrual bleeding such as menstrual pads.

It is another object of the present invention to offer a device capable of assuring prevention of blood leakage regardless of the anatomical size, shape, changing of direction and of lumen contour of the vagina, as a result of remarkable adaptability to anatomical size, shape, contour of the vagina, and adaptability to contingent changes of size, shape, lumen contour of the vagina, to maintain its outer surface in close contact with the vaginal mucosa and offer a sealing closure to blood in any condition.

It is another object of this invention to propose an inflatable cup shaped device capable of reliably achieving prevention of leakage of menstrual blood while being easy to be worn, conceivably adding no discomfort to the female user, by gently applying upon the vaginal mucosa a pressure just barely sufficient to prevent passage of blood between the device and the vaginal mucosa, such a pressure being generally proportional to the pressure, notoriously negligible, exerted by menstrual blood.

It is another object of this invention to propose an inflatable device capable of reliably achieving prevention of leakage of menstrual blood, while being easy to insert and likewise easy and comfortable to extract.

It is another object of the present invention to provide an intravaginal device capable of preventing, when indicated, leakage or outflow, in any amount, of organic fluids in general, besides blood, from the vaginal orifice.

It is an object of the present invention to provide an inflatable intravaginal device offering means of prevention of significant hemorrhage in cases for instance of pathological bleeding, by reliably preventing excessive blood loss from the vagina, by limiting the amount of blood extravasation to an amount not exceeding the maximum capacity of reservoir of a tract of the vagina proximal to the site of placement of said inflatable device, as a result of a blockage exerted by such inflatable intravaginal device on the vaginal transit of blood. A device of this kind may prevent the serious medical complications associated with massive vaginal-uterine bleeding and at times may well be a life saving device.

It is another object of this invention to provide an inflatable cup shaped device capable of functioning as reservoir for the blood exiting from the cervical os.

It is an object of the present invention to provide an inflatable menstrual cup capable of changing size due to its inflatability. Due to its significantly reduced size when deflated the device is easy to insert and extract from the vaginal orifice without causing any discomfort to the female user experienced by the users of the priorly cited menstrual cups.

It is an object of the present invention to provide an inflatable menstrual cup capable of automatic sealable closure of its opening on extraction so as to not allow escape of blood from the collector cup at the time of extraction and disposal.

It is another object of the present invention to provide an intravaginal inflatable member for the prevention of leakage of blood from the vagina canal with an applicator, the plunger of the applicator being capable of actuating variuos type of pneumatic sources to inflate the inflatable member.

DRAWING FIGURES

FIGS. 9 through 14 show a pneumatic pressure delivery device incorporated into a vaginal tampon applicator at different stages of operation.

FIG. 15 shows the device of FIG. 2 shown in situ, i.e. inserted and resting inside the vaginal canal and accomplishing the function of impeding exiting of blood from the vaginal orifice.

FIG. 17 is a prospective view of a part the device of FIG. 16.

FIG. 18 is a prospective view of another part the device of FIG. 16.

FIG. 19 is a prospective view of another part the device of FIG. 16.

FIG. 20 is a cross section view of the lower chamber of the device of FIG. 16 showing an inflating apparatus.

FIG. 20A is a cross section view of the lower chamber of the device of FIG. 16 showing an alternative type of inflating apparatus similar to the inflating apparatus shown in FIG. 20.

FIG. 21 is a cross section view of the lower chamber of the device of FIG. 16 showing an alternative type of inflating apparatus.

FIG. 30 is a side view of an alternative form of the inflatable member associated with an absorbent member as it appears after inflation.

FIG. 31 is a cross section view of an inflatable member associated with an absorbent member housed within an applicator prior to inflation and insertion into the vaginal canal.

FIG. 31A is a top view of a detail of the device of FIG. 31.

Figure 40:
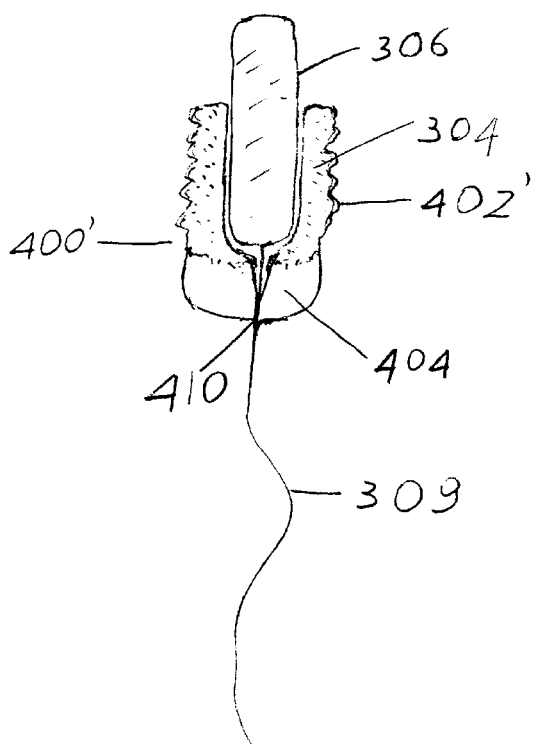
FIG. 40 is a cross section view of an alternative form of the device of FIGS. 33 and 34 combined with a tampon as it appears prior expansion.
Figure 40A:
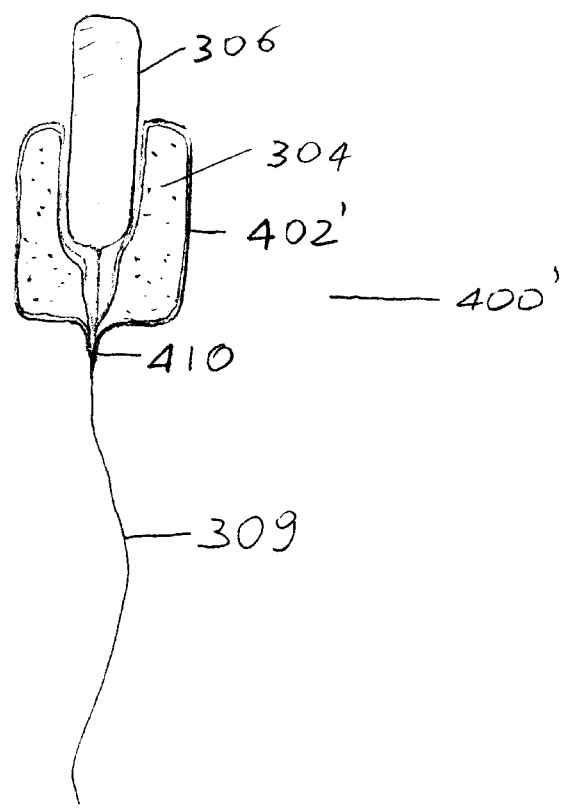
FIG. 40A is a cross section view of an alternative form of the device of FIG. 40 as it appears after inflation.
Figure 41:
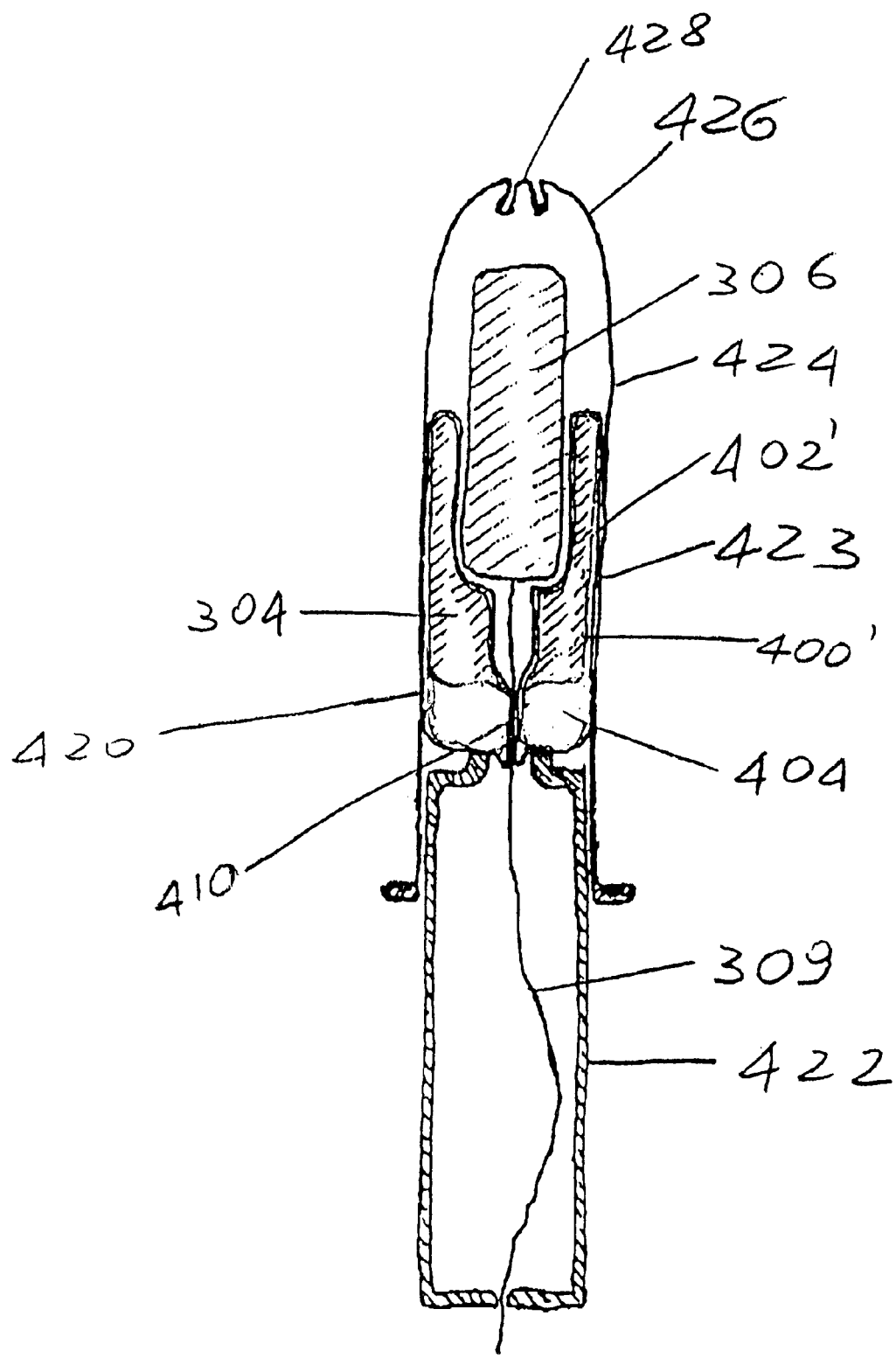

FIG. 41 a cross section view of the device of FIGS. 40 and 40A within an applicator prior to ejection into the vagina.

DETAILED DESCRIPTION OF THE INVENTION

Figure 1:
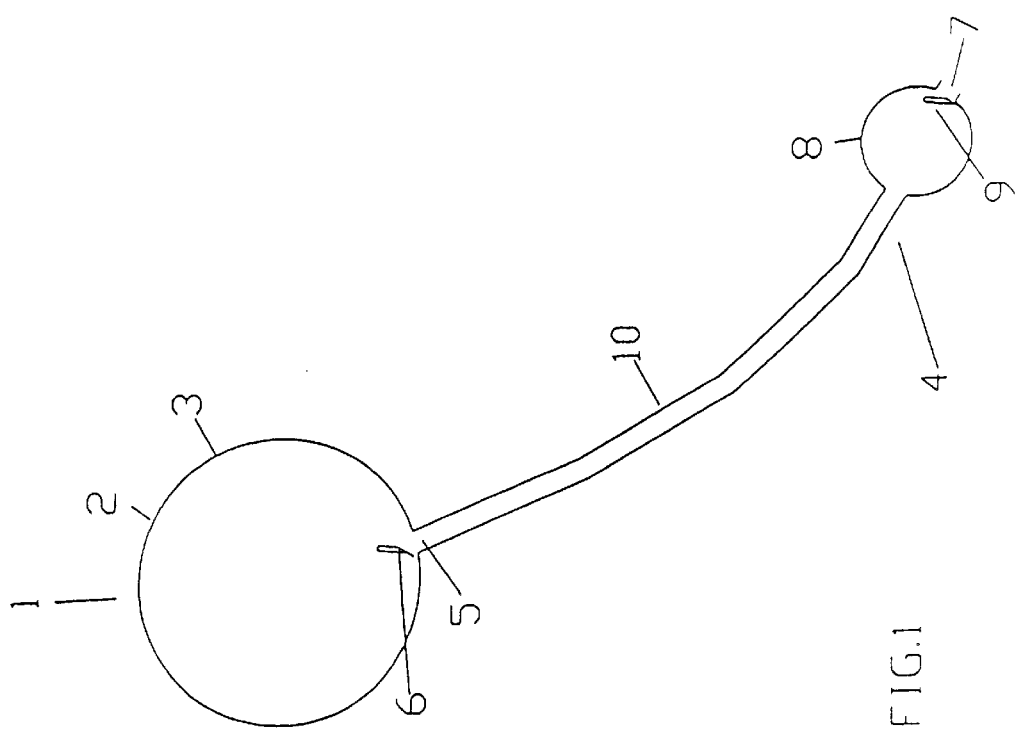
FIG. 1 is a side view of the device as it appears in operation, i.e. after inflation.

A typical embodiment of the invention is illustrated in FIG. 1. The device generally indicated at 1 is composed of an inflatable or expandable member or means or balloon 2 and pneumatic pressure delivery system or inflating means 4.

Balloon 2 has walls 3, unidirectional valve 6, which can be constructed as a pivoting flap, operating inlet 5 of tubular member or conduit 10 of inflating means 4. Inflating means 4 is composed of pressure delivery source or pump 8 with air intake opening 7 provided with unidirectional pivoting flap valve 9, and tubular member or conduit 10 connecting pump 8 to balloon 2 via valve inlet 5 through unidirectional valve 6.

Balloon 2 can be made of material substantially impermeable to fluids.

Inflatable member 2 may be coated with a suitable means which by interfacing between the balloon and the vaginal walls provides reversible sealing with the vaginal walls as it will be disclosed in the description of the operations.

Such interfacing means could include filtering means which selectively allows passage of air or suitable gas while preventing passage of blood or organic fluids.

The inflatable member 2 can be constructed as a self-deflatable member after a predetermined time of inflation.

Such a feature can be achieved with micro porous material allowing air to escape from the inflatable member after inflation at a substantially predetermined rate of a change in permeability to air of a suitable material included in said inflatable member, said change in permeability allowing air to escape from the inflatable member at a substantially predetermined time following inflation of the inflatable member.

Figure 4:
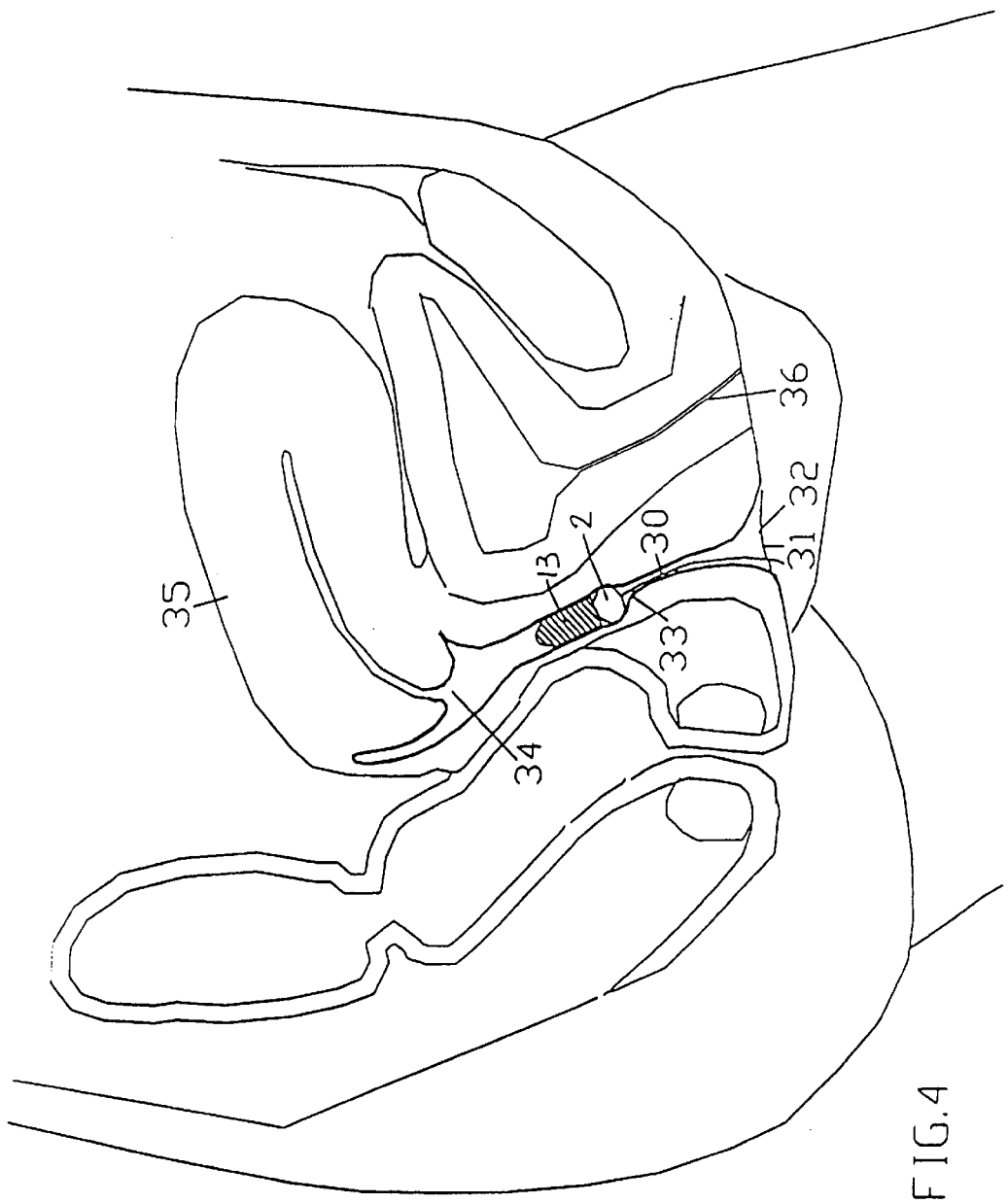
FIG. 4 is a cross sectional view of the human female pelvis.

In operation balloon 2 is inserted by the operator or user in vagina in a deflated status. As shown in FIG. 4, balloon 2, once inserted into the vaginal canal or vagina 30 beyond vaginal orifice 32, is inflated by the operator-user by means of pumping air or other suitable gas or fluid inside balloon 2 via conduit 10 by acting on pump 8. Balloon 2 will be expanded by the user-operator acting on pump 8 until wall 3 of balloon 2 become in contact, in an expanded status, with vaginal walls 33 of vagina 30.

Balloon 2, when expanded, will not permit exit of any organic fluid such as blood from vagina 30 by sealing the walls 33 of vagina 30 to walls 3 of balloon 2. Indeed expanded balloon 2 obliterates the space between balloon walls 3 of balloon 2 and, vaginal walls 33. Balloon 2 is easily extracted from the vaginal orifice 32 by pulling on conduit 10 or alternatively by pulling on other means such as a string connected to balloon 2. The operator or user, by pulling on conduit 8 or on the just described string, will decrease the transverse diameter of balloon 2, facilitating its exit from vaginal orifice 31.

Figure 2:
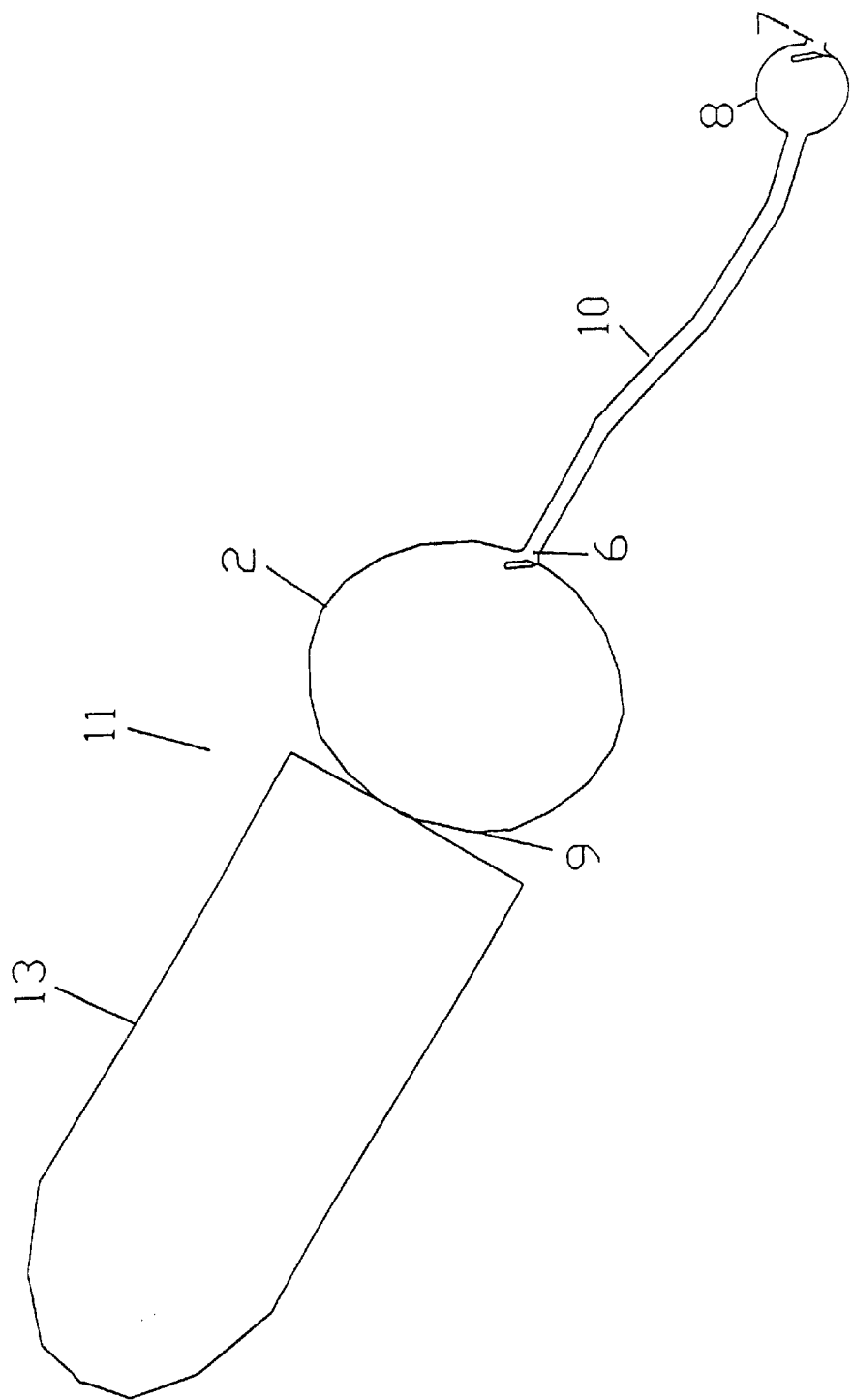
FIG. 2 is a side view of an alternative form of the device shown after inflation.

FIG. 2 shows another version of the device, generally indicated at 11. In this version balloon 2 is connected to blood absorbing means or vaginal tampon 13. The device is operated exactly as device 1. Tampon 13 will provide absorbent action for the blood. Blood which escapes tampon 13 is impeded to exit from vaginal orifice by expanded balloon 2.

Figure 3:
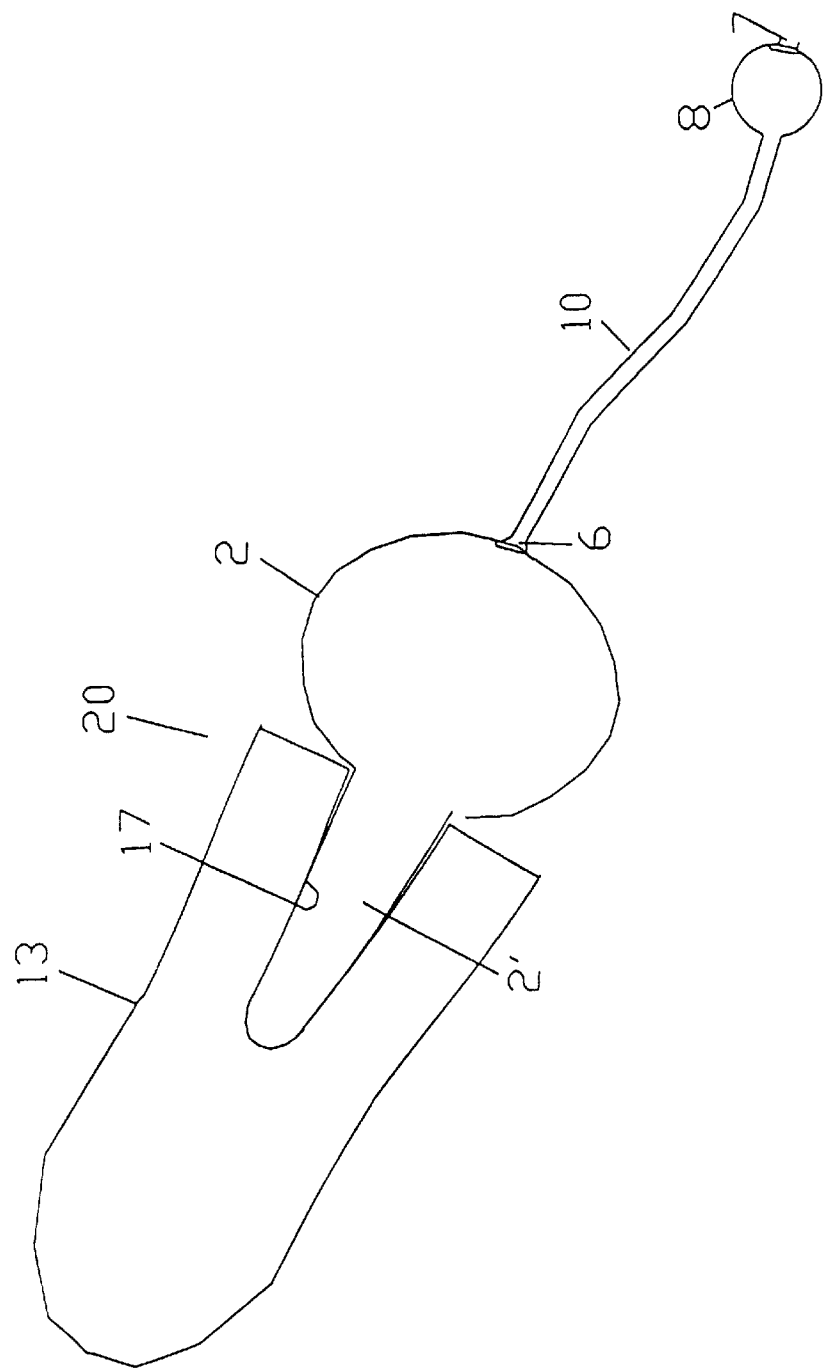
FIG. 3 is a side view of an alternative form of the device shown after inflation.

FIG. 3 shows another version of the device, generally indicated at 20. In this version balloon 2 has extension 2' engaging correspondent recess 17' of blood absorbing means or tampon 13.

In use, after insertion in vagina, balloon 2 is inflated as described for devices 1 and 11. Balloon extension 2' will also inflate as soon as tampon 13 will soften due to absorbency of blood providing little resistance to radial expansion of extension 2' of balloon 2. In this device, tampon 13, being pressed against wall 33 of vagina 30 by the expanded extension 2' of balloon 2, will contribute to the sealing by obliterating any gap between tampon 13 and vaginal walls 33. Balloon 2, as in the two other described devices, will provide sealable closure of vaginal canal 30.

Figure 5:
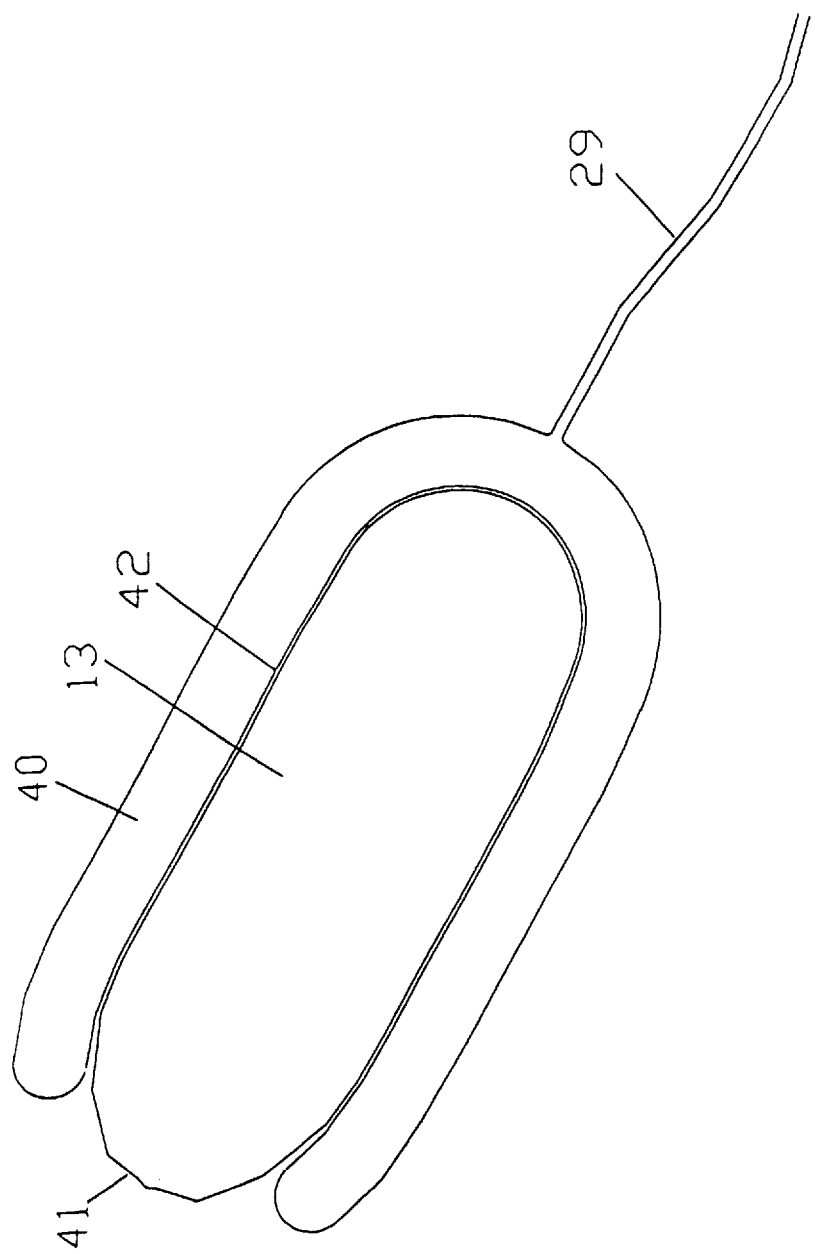
FIG. 5 is a side view of an alternative form of the device shown after inflation.

FIG. 5 shows yet an alternative form of the device, where balloon 40 is cup-shaped harboring tampon 13. In this version blood will be forced to enter distal end 41 of tampon 13 as balloon 40 encircles tampon 13 except in correspondence of distal end 41 of tampon 13, sealing side 42 of tampon 13.

Figure 6:
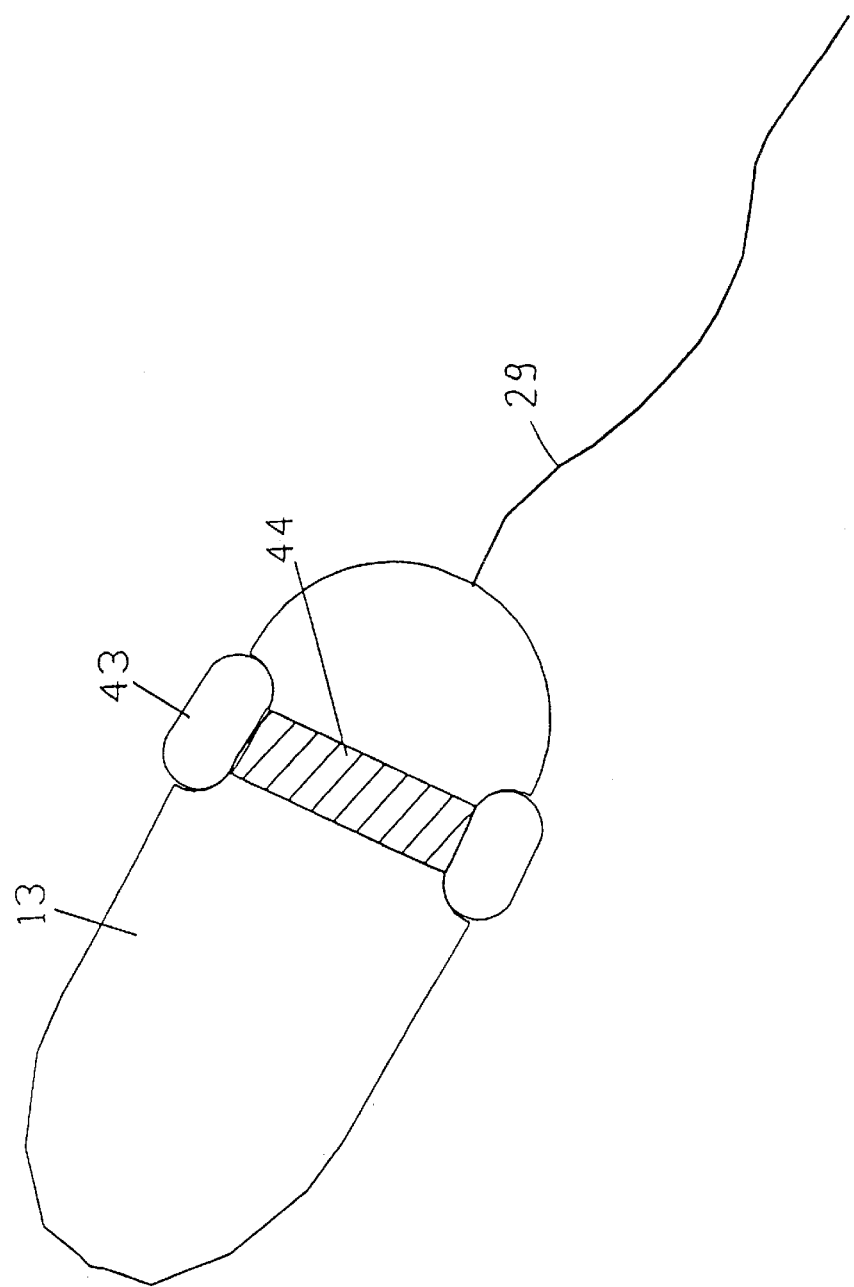
FIG. 6 is a side view of an alternative form of the device shown after inflation.

FIG. 6 shows an embodiment where the inflatable member 43 is concentric to, and sealed to, a segment 44 of any intravaginal menstrual blood absorbing means or tampon 13, where said segment 44 is adapted to be impermeable to fluids. In such an embodiment the inflatable member 43 expands to exert a pressure on the vaginal walls 33 of vagina 30 to seal to fluids the space between the inflatable member 43 and the vaginal walls 33, providing, in combination with the adapted segment 44 of a tampon 13, for a blockage to vaginal transit of menstrual blood or organic fluids.

Figure 7:
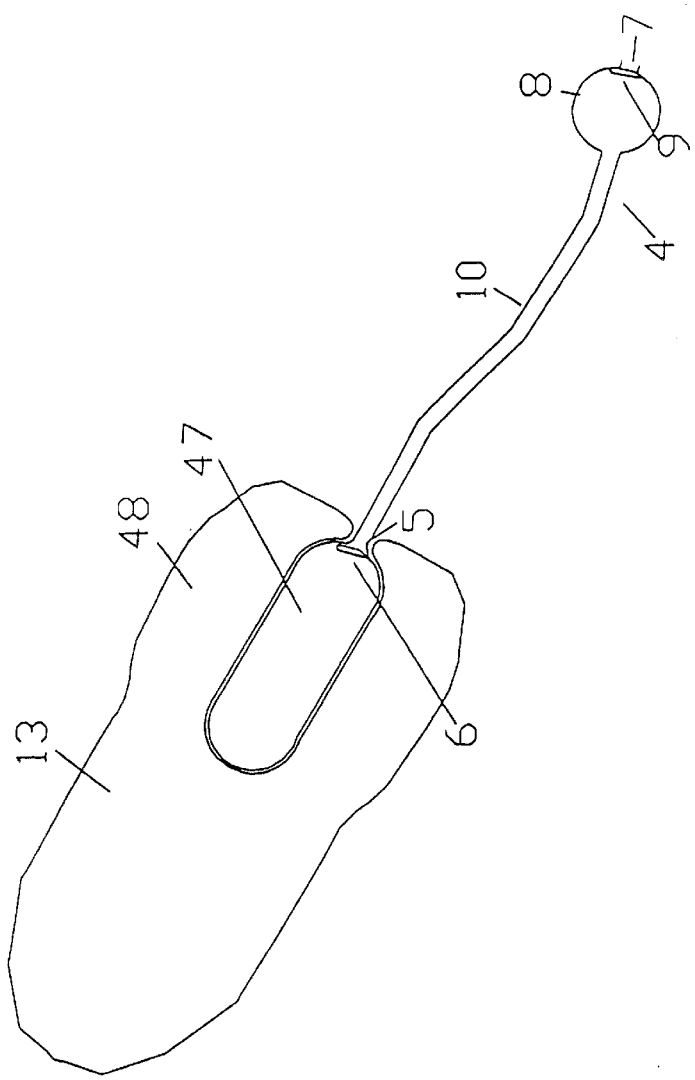
FIG. 7 is a side view of an alternative form of the device shown after inflation.

FIG. 7 shows another embodiment of the device where balloon 47 is contained in its entirety within tampon 13.

In use, once balloon 47 is inflated, it will press on corresponding overlying segment 48 of tampon 13 closing the gap between vaginal walls 33 and tampon 13 by compressing segment 48 to the extent of preventing any leakage of blood.

Figure 8:
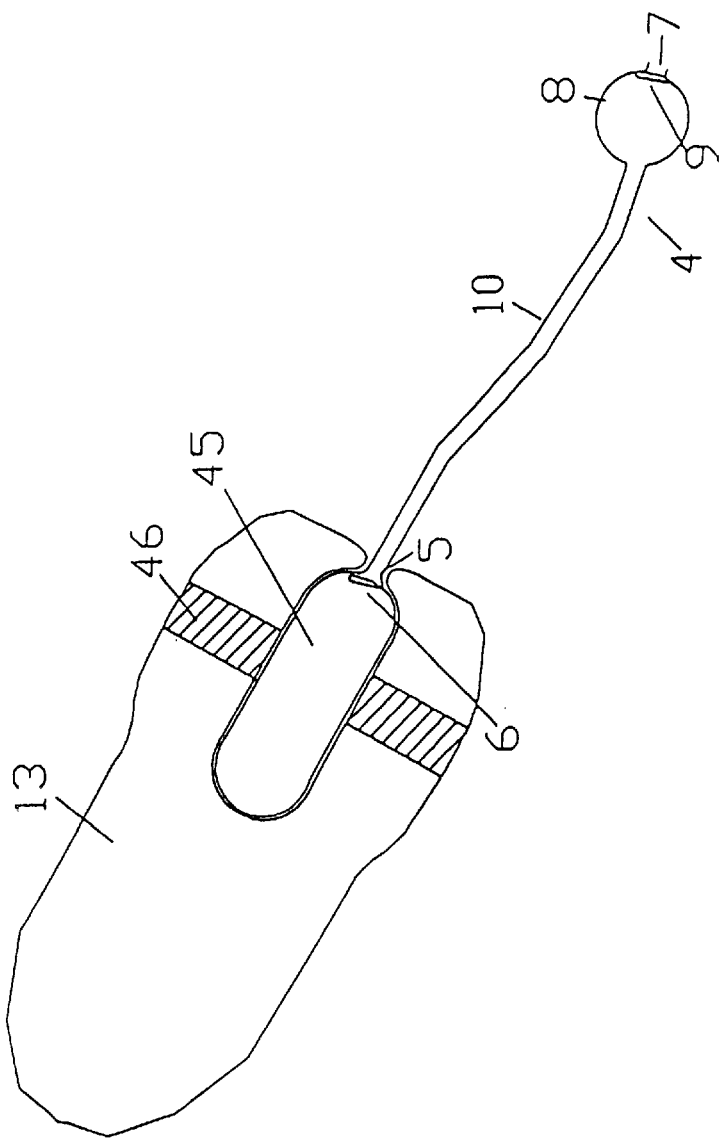
FIG. 8 is a side view of an alternative form of the device shown after inflation.

FIG. 8 shows another embodiment, where the intravaginal inflatable member 45, substantially impermeable to fluids, is contained in the interior of a segment 46 of a tampon 13. The segment 46 is adapted to be substantially impermeable to fluids. The inflatable member 45 expands to exert a pressure on the vaginal walls 33 via segment 46 of tampon 13 to seal to fluids the space between segment 46 of tampon 13 and vaginal walls 33, so as to provide, in combination with the adapted segment 46 of tampon 13, a blockage to the vaginal transit of menstrual blood.

FIG. 9 shows a pneumatic pressure delivery system or applicator-inflator 50 comprising a standard tampon applicator 51 which incorporates a syringe 52. Operator, after inserting tampon applicator 51 into vagina 30, press on syringe barrel 53, which telescopically slides within applicator barrel 51 to eject tampon 13 with its connected balloon 2 into the vaginal canal 30. FIGS. 10 and 11 illustrate the insertion and delivery of tampon 13 with its connected balloon 2. As shown in FIG. 12 the user-operator, after having fully advanced syringe barrel 53 on applicator barrel 51, will act on syringe plunger 54, inflating balloon 2. As shown in FIG. 14, upon full inflation of balloon 2, further advancement of syringe plunger 54 will result in a disengagement of applicator-inflator 50 from tampon 13 and its connected balloon 2.

As shown in FIG. 15, tampon 13 with balloon 2, rests firmly in vaginal canal 30, providing sealable closure of the canal, preventing any blood leakage.

Figure 16:
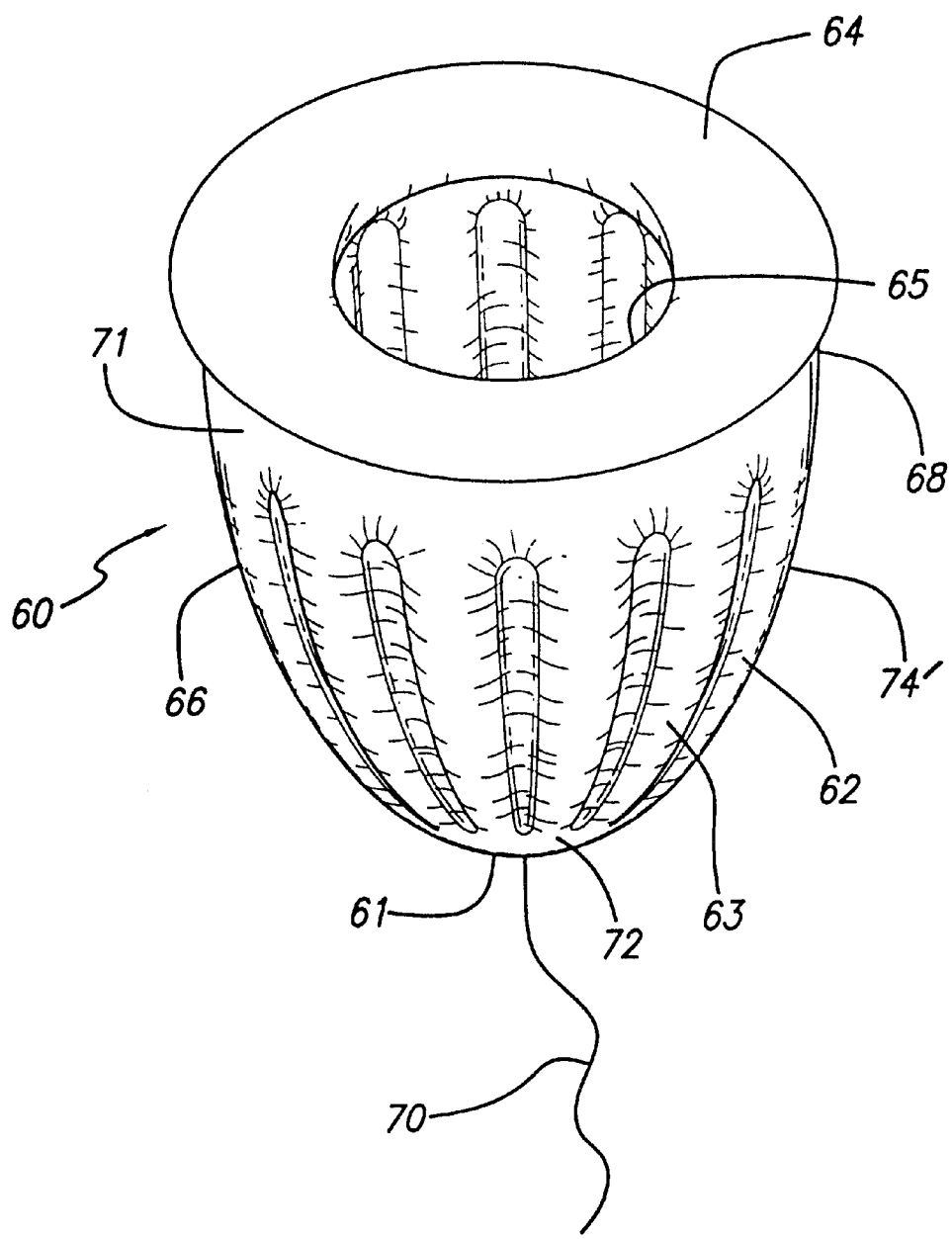
FIG. 16 is a side view of an alternative form of the device as it appears in operation, after inflation.
Figure 23:
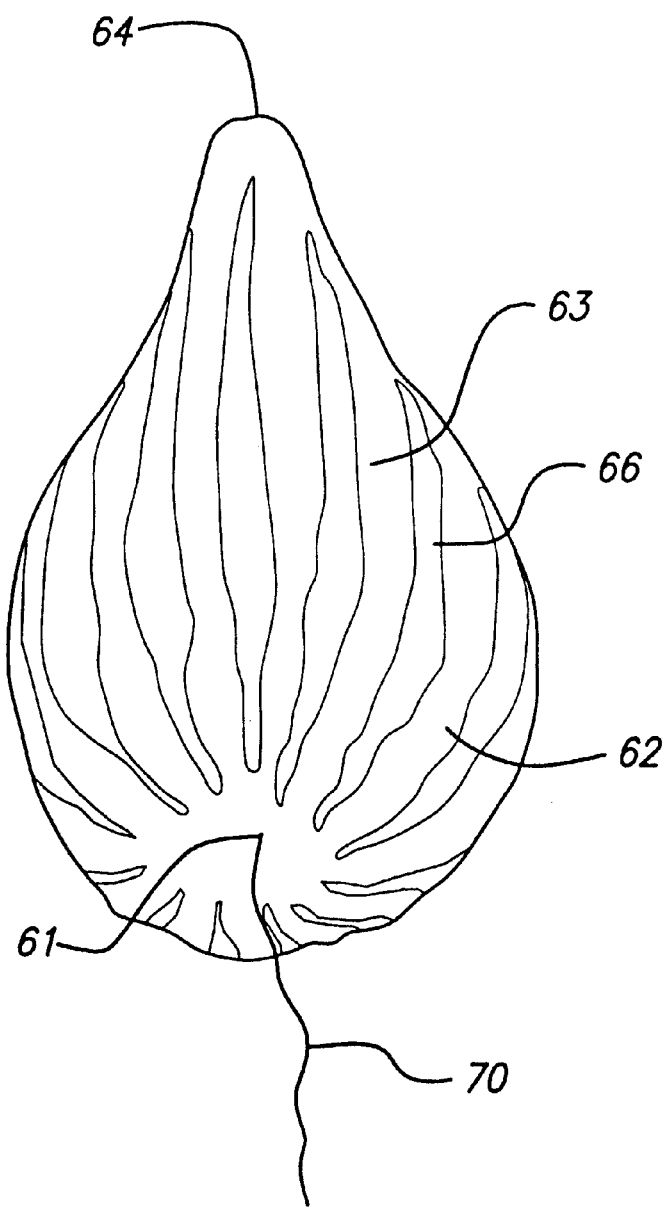
FIG. 23 is a side view of the device of FIG. 16 deflated, with blood collected and sealed off, ready to be extracted.

FIG. 16 shows an alternative form of the cup-shaped inflatable device of FIG. 5 in use after inflation. As shown in FIGS. 16, 17, 18 and 19, the device generally indicated at 60 is a cup-shaped or inverted dome shaped member composed of inflatable, generally concave, reservoir or inflatable body means 62 for providing a collection site of menstrual blood and inflatable donut shaped member 64 sealingly connected to reservoir 62 at rim 68 and 68' of reservoir 62 as better seen in FIGS. 17 and 18. Both reservoir 62 and donut shaped member 64 are made of substantially gas and fluid impervious material. Cup shaped member 60 has, superiorly, circular opening or mouth 65 delimited by donut shaped member 64, and has, inferiorly, pole 61 through which exits, or to which is connected, string 70. As best seen in FIGS. 17 and 19 reservoir 62 is made of two generally concave or cup shaped thin sheets parallelely arranged, respectively interior wall 74 and exterior wall 74' of substantially non compliant material impervious to gas and fluids. Reservoir 62 is composed of a series of elongated chambers 63 regularly spaced and separated one from another by sealed segments 66 obtained for example by thermally fusing interior wall 74 and exterior wall 74' at regular intervals. Chambers 63 are in flow communication superiorly via upper common chamber 71 with the interior of inflatable donut shaped member 64 and inferiorly they are in flow communication with lower common chamber 72. Donut shaped member 64 is made of substantially resilient impervious compliant material such as, for instance, rubber. With device deflated at rest prior to inflation or at the time of extraction, as shown in FIG. 23, donut member 64, retracts centripetally as a result of its resiliency, sealingly closing circular opening or mouth 65, not allowing escape of the collected blood at time of removal as it will be described below.

Inflatable cup shaped member 60 can be inflated as all the previously described devices of FIGS. 1 to 15 via an external source of pneumatic means i.e. inflating means, such as for instance a syringe or a bladder, connected to the device via a tubular member or conduit, or can be inflated via internal source of pneumatic means, i.e. internally located within the device, as illustrated in FIGS. 20, 20A and 21. FIG. 20 shows a type of apparatus of pneumatic source means of inflation housed within the inflatable member.

Lower chamber 72 houses bladder 67 having wall 111 made of material substantially impermeable to fluid but not to gasses such as air or $CO_2$. Bladder 67 preferably adheres to segment 77 of interior wall 74 and has internal breakable membrane or diaphragm 82 made of material less resistent to pressure than the material of wall 111, separating upper compartment 81 from lower compartment 87. Compartment 81 and 87 contain components chemically reacting to produce pneumatic means of inflation such as air, $CO_2$ or any suitable gas. For instance upper compartment 81 may contain an acidic fluid solution 90, such as a solution of citric acid or malic acid or any other suitable acidic solution and lower compartment 87 contains effervescent substrate 89 such as sodium bicarbonate or any suitable substrate mixable with the acidic solution 90 contained within upper compartment 81 of bladder 67 to generate pneumatic means of inflation or gas, such as CO2.

As better shown in FIG. 20, string 70 is anchored via segment 70' to segment 77 of interior wall 74 of reservoir 62, slackly traverses lower chamber 72 to adhere via segment 70" to internal surface of exterior wall 74' of lower chamber 72 and sealingly exits through exterior wall 74' in proximity of pole 61 of reservoir 62.

In use, the female user compresses bladder 67 between her finger. Since closed upper compartment 81 of bladder 67 is filled with fluids, the pressure applied upon it will result into rupture of membrane 82 which is made of less resistent material than the wall of bladder 67. Rupture of membrane 82 allows mixing of acidic solution 90 with effervescent substrate 89. Upon mixing of acidic solution 90 with substrate 89, CO2 or any other suitable gas will be generated. Being wall of bladder 67 made of material permeable to gasses, CO2 or the generated gas will enter and diffuse within reservoir 62 and donut shaped member 64 which will inflate up to sealingly engage the wall of the vagina. The device fully inflated will appear as shown in FIG. 16. Blood flowing from the cervical os will be collected within reservoir 62 and no leakage will occur due to the fact that donut shaped member 64 and reservoir 62 sealingly engage the vaginal wall. Once the female user wants to extract cup shaped member 60 from the vagina she will pull on string 70. The pulling of string 70 will cut through exterior wall 74' creating a slit through which CO2 or other suitable gas can escape. Due to the impermeability to fluids of wall of bladder 67, the residual acidic solution and substrate will remain within bladder 67 and will not be spilled into the vagina. Donut shaped member 64, due to its intrinsic resilient properties will centripetally retract closing circular opening 65 not allowing any spillage of blood upon extraction.

FIG. 20A shows an alternative form of inflating apparatus for the mixing of acidic solution 90 with substrate 89. This apparatus is in all similar to inflating apparatus of FIG. 20, except for an additional element, string 105. String 105 is firmly attached along a diameter of membrane 82, traverses lower chamber 72 to sealingly exit through invaginated portion 107 of exterior wall 74'. In use, in devices supplied with string 105, the female user ruptures membrane 82 by pulling on string 105, which upon traction will cut through membrane 82 creating a slit which leads to mixing of acidic solution 90 with substrate 89. Subsequent steps are identical as for the device with inflating apparatus shown in FIG. 20.

FIG. 21 shows yet an alternative type of apparatus of internal pneumatic source in all similar to the apparatus illustrated in FIG. 20 with the folllowing differences.

Acidic solution 90 and substrate 89 are no longer present. Bladder 67 is replaced by capsule or container 67' which is void of membrane 82. Capsule 67' has wall 113 and a weaker portion 112 of said wall, positioned in correspondence of puncher 86.

Wall 113 of capsule 67' is made of material impermeable to gasses and contains compressed pneumatic means or gas 110, such as CO2 or air. Perforating puncher 86 is attached via flexible arm 87 to the wall 113 of capsule 67', as clearly shown if FIG. 21.

In use, the female user prior to inserting the device into the vagina will press on pole 61 of wall 74 to puncture membrane 112 of capsule 67' and permit passage of gas 110 or other suitable gas from capsule 67' into reservoir 62 and donut shaped member 64 which will inflate up to sealingly engage the wall of the vagina.

Alternatively, as shown for the device of FIG. 5, inflatable cup shaped member 40 is inflated by an external source of pneumatic means i.e. inflating means such as for instance a syringe or a bladder via tubular member or conduit 29. Alternatively an external source of pneumatic means applicable to all disclosed devices comprises a capsule containing compressed air or CO2 or any suitable gas or a bladder containig components chemically reacting to produce the pneumatic means such as CO2 or any suitable gas, said gasses delivered to the inflatable member via a conduit such as conduit 29 of FIG. 5.

Figure 24:
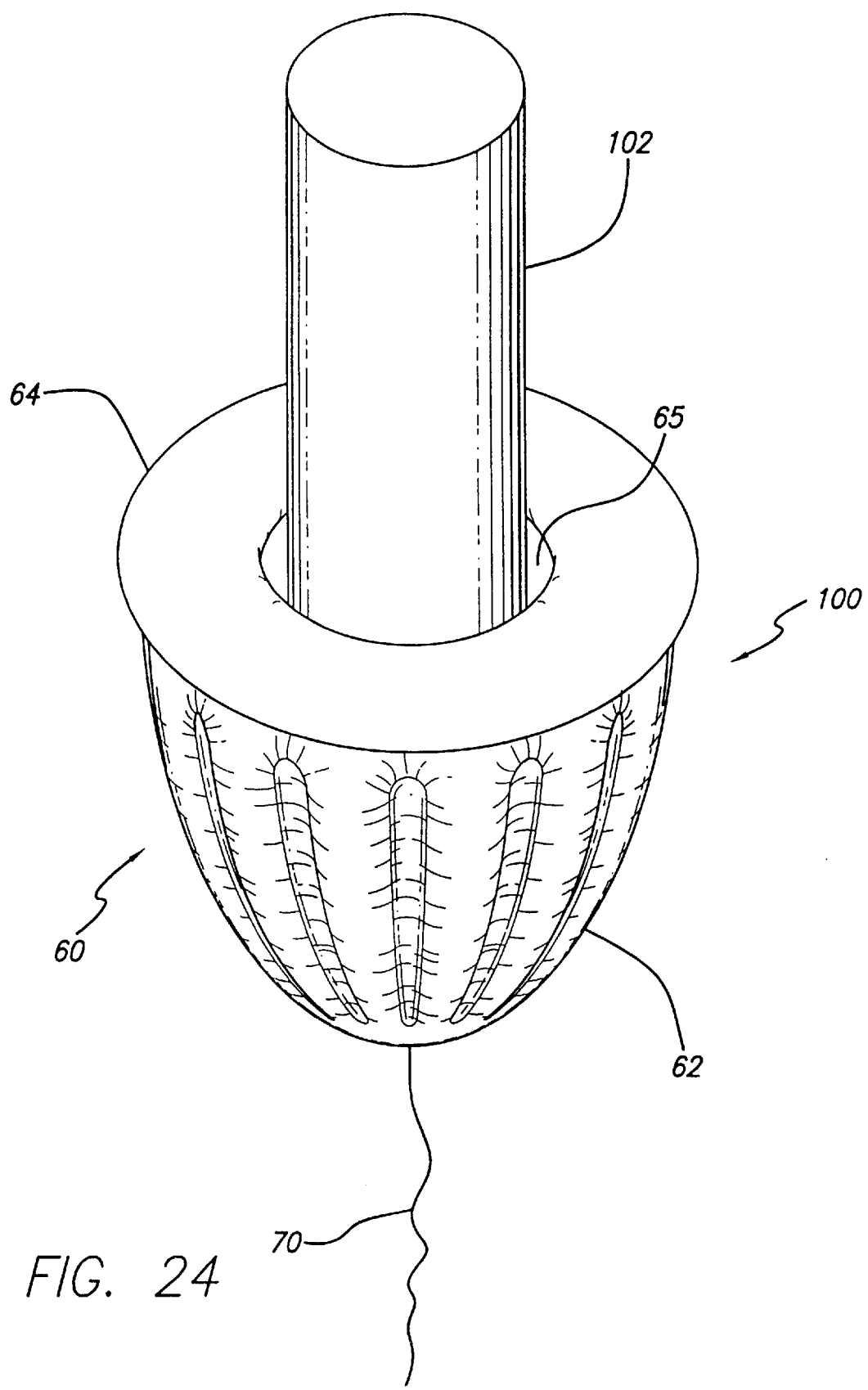
FIG. 24 is a side view of an alternative form of the device associated with a tampon, shown after inflation.
Figure 25:
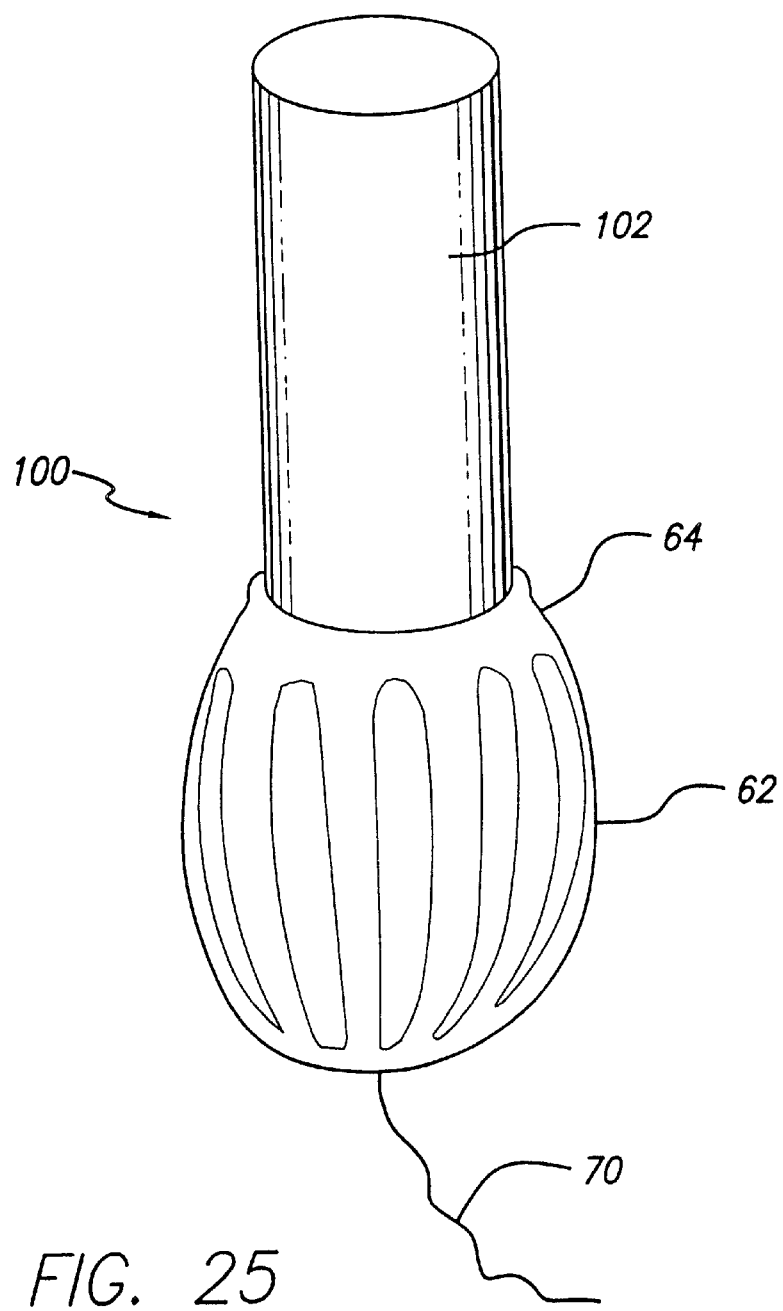
FIG. 25 is a side view of the device of FIG. 24 shown deflated, with blood collected and sealed off, ready to be removed.

FIGS. 24 and 25 show an alternative form of the device of FIGS. 16 through 21 and FIG. 23. The device generally indicated at 100 is composed of the same cup shaped member 60 and of tampon or absorbent member 102. Tampon 102 is connected to cup shaped member 60. The device is used exactly as device 60 of FIG. 16. Absorbent member 102 will absorb blood while cup shaped member 60 will collect the blood escaped from absorbent member 102. As shown in FIG. 25, at time of extraction donut shaped member 64 will circularly retract around tampon 102 not allowing escape of blood collected within reservoir 62.

Figure 22:
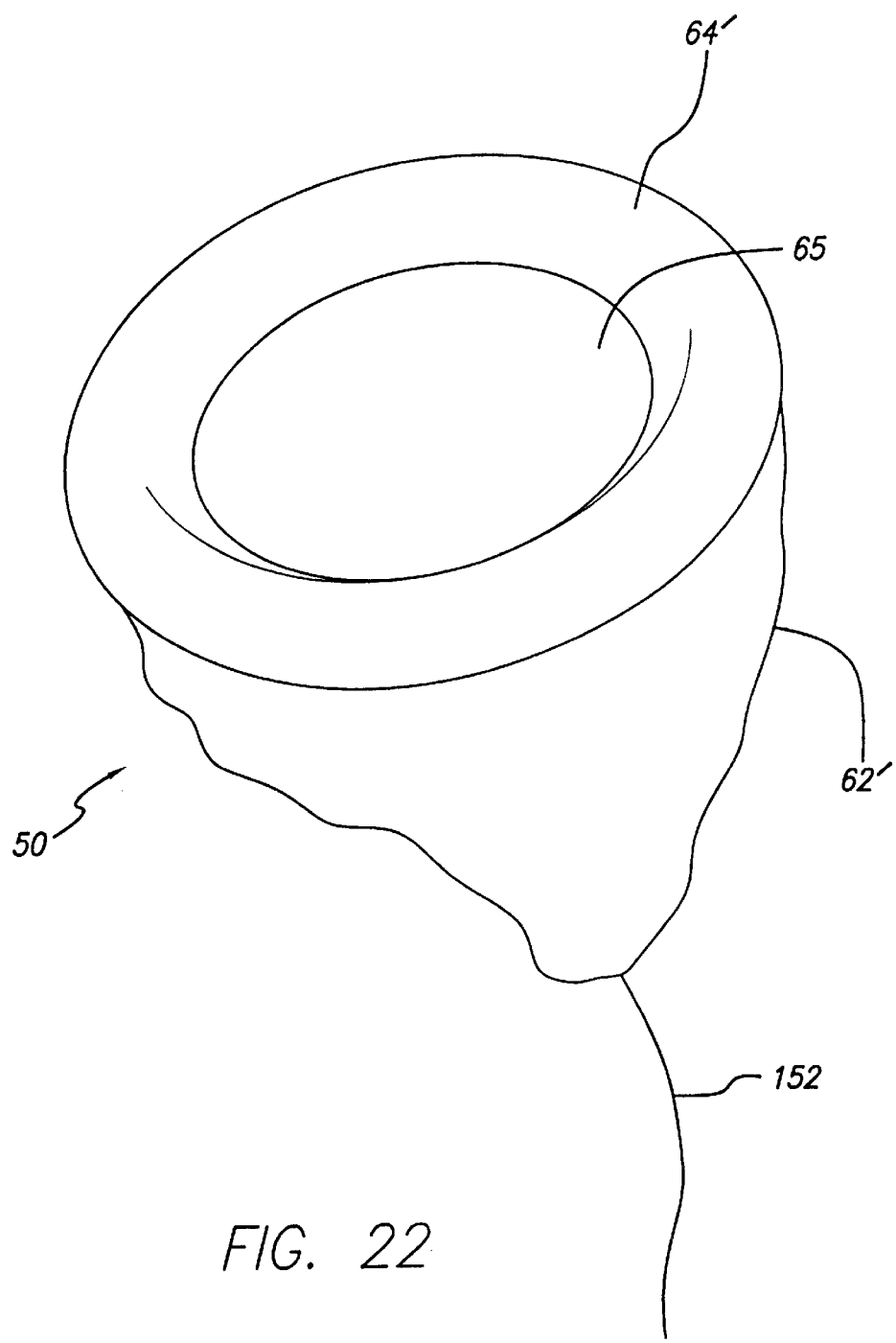
FIG. 22 is side view of an alterrnative form of the device shown in operation after inflation.

FIG. 22 shows an alternative form of the device of FIGS. 16 through 21 and FIG. 23. The device generally indicated at 150 is composed of a generally donut shaped inflatable member 64' to which is connected reservoir or pouch or bag or body means 62' for the collection of menstrual blood. In this device, reservoir or body means 62' is no longer inflatable being made of a thin sheet of flexible substantially impermeable material attached, as above disclosed, to donuut shaped member 64. Device 150 is provided with striing 152 attached to pole 154 of reservoir 62' for removal of the device.

Donut shaped member 64 can house any of the inflating apparatuses described in FIGS. 20, 20A and 21 with annexed strings or can be inflated by an external pneumatic source as for the device of FIG. 5. Inflation and deflation of donut shaped member 64 is accomplished as for the devices of FIG. 16 to FIG. 23. An absorbent member can be harbored within the device as for the devices of FIG. 5 and FIGS. 24 and 25.

Figure 26:
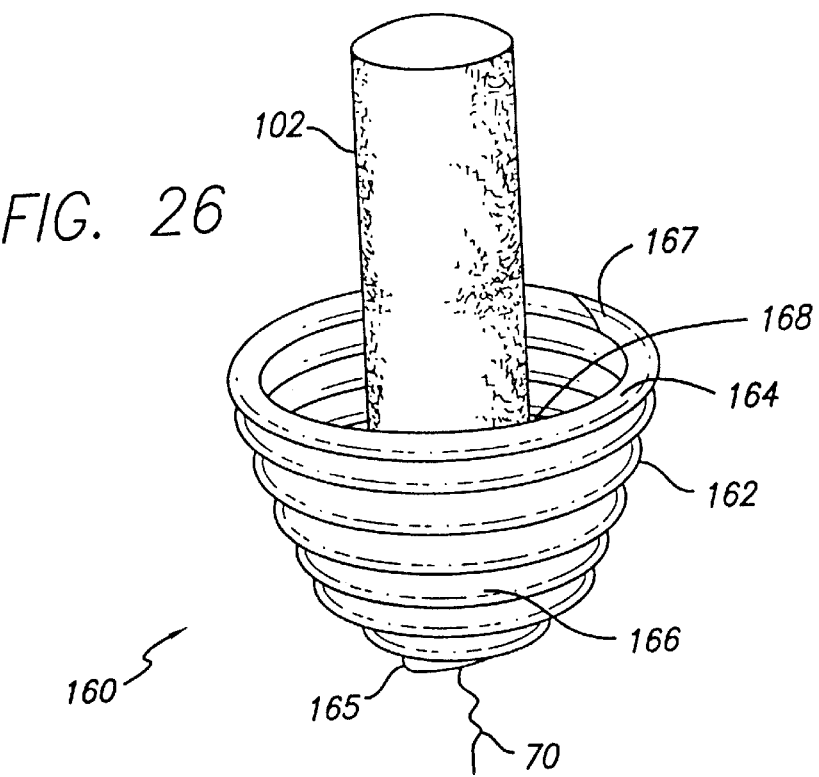
FIG. 26 is a side view of an alternative form of the device as it appears in operation after inflation.

FIG. 26 shows an alternative form of the device of FIGS. 16 through 21 and FIG. 23. In this device, generally indicated at 160, cup shaped inflatable member or reservoir or body means 162 is composed of inflatable substantially impermeable tube 164, made either of resilient material such as rubber or polyurethane or of a not compliant material, arranged in a coils where spires 166 are sealingly connected to each other or are connected via an impermeable connecting membrane.

Spires 166 of tube 164, as arranged, form a wall delimiting cavity 168 for the collection of menstrual blood. Proximal end 165 of tube 164 can house the pneumatic source means of inflation such as the ones described in FIGS. 16 through 21. Distal end 167 of tube 164 is sealed to avoid escape of gas. Cup shaped member 162 can house absorbent member 102.

As for the previously described devices, device 162 is inflated either by the pneumatic source means of inflation housed within the inflatable coiled tube 164 or by a connected external pneumatic source. The device is inserted into the vagina and extracted as the previuosly described devices.

Figure 27:
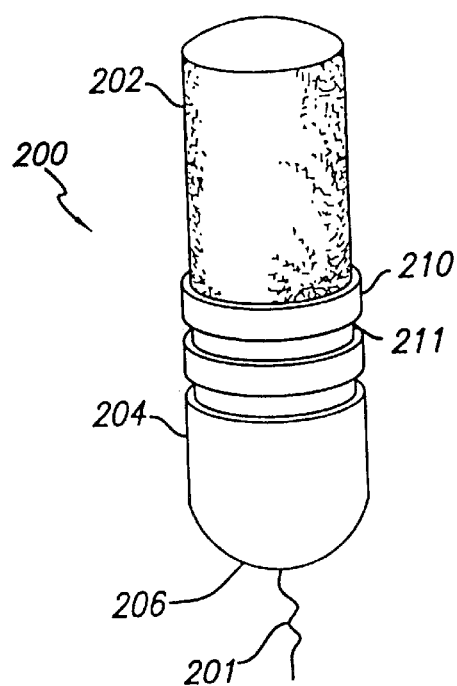
FIG. 27 is a side view of an alternative form of the inflatable member in combination with an absorbent member as it appears before inflation.
Figure 28:
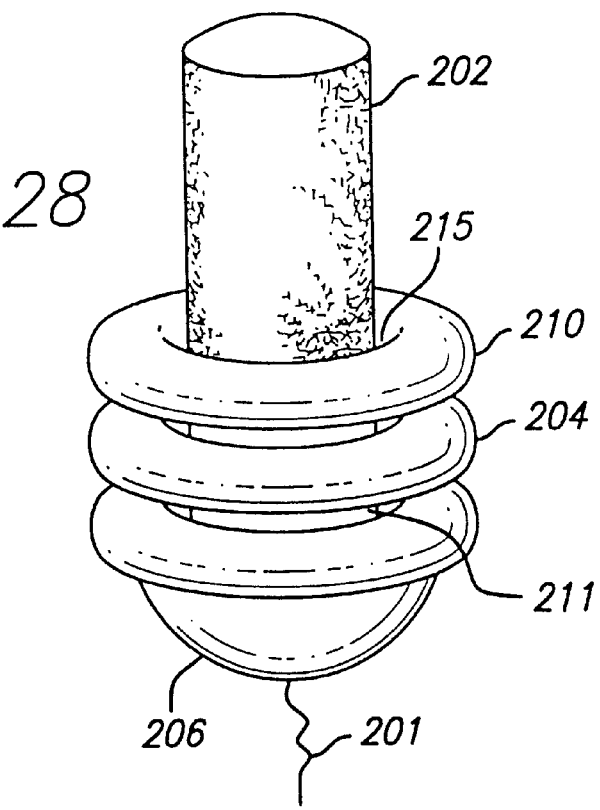
FIG. 28 is a side view of the inflatable member in combination with the absorbent member of FIG. 27 as it appears after inflation.
Figure 29:
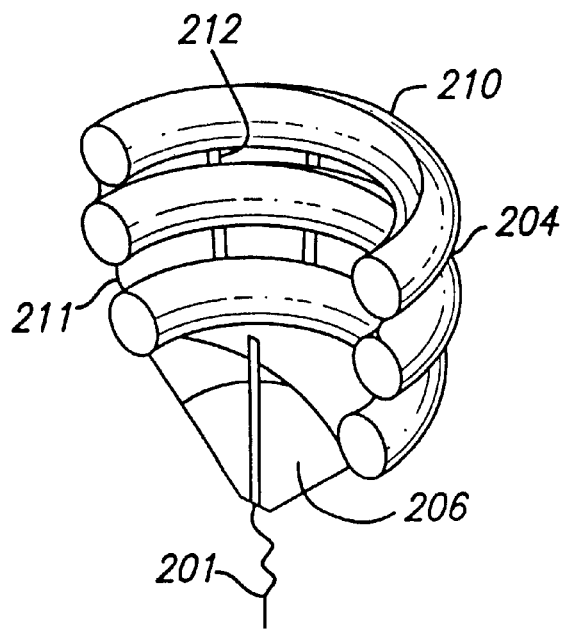
FIG. 29 is a cross section view of the inflatable member of FIG. 27 alone without tampon as it appears after inflation.

FIGS. 27, 28 and 29 show an alternative form of the inflatable member combined with an absorbent member. As shown in FIG. 27 the device generally indicated at 200 is composed of absorbent member or tampon 202 generally of cylindrical shape and inflatable member or menstrual cup 204 similar in shape and function to inflatable member 60 of FIGS. 16, 17, 18, 19, shown, prior to use, deflated, partially enveloping the lower segment of absorbent member or tampon 202. String 201 is connected to bottom of device 200. Inflatable member 204 is substantially impermeable to fluids and gasses. As better shown in FIG. 29, which is a cross section of inflatable member 204 alone without tampon 202, inflatable member 204 is formed in its lower end with chamber 206. Chamber 206 house any of the pneumatic source means of inflation shown in FIGS. 20, 20A and 21 and above disclosed in page 9 and 10. Inflatable member or cup 204 is composed of one or more circular chambers 210, joined together by membrane 211, in flow communication with each other via conduits 212 as better shown in FIG. 29 and with lower chamber 206. As shown in FIG. 28, once inflated, inflatable member 204 assumes the shape of a cup with reservoir 215. Device 200 is designed to prevent leaking of blood from the vagina. While absorbent member or tampon 202 absorbs blood, inflatable member or cup 204 has the dual function of collecting via reservoir 215 the menstrual blood escaped to tampon absorption and that of sealing the vaginal canal.

FIG. 30 shows an alternative form of the device generally indicated at 220. In this version inflatable member 221 also cup shaped encircles tampon 202 as inflatable member 204 of device 200, with the difference that inner surface or membrane 222 of inflatable member 221 is sealed to the surface of lower segment of tampon 202 before and after inflation lacking therefore of a reservoir.

Chamber 223 houses at the bottom end of inflatable member 221 any of the pneumatic means of inflation or source means of gas disclosed in page 9 and 10 and illustrated in FIGS. 20, 20A and 21.

FIG. 31 shows an inflatable member connected to a tampon, both housed within an applicator which has the dual function of carrying, inserting and delivering the device into the vagina and that of actuating the inflation of the inflatable member. The device generally indicated at 230 is composed of vaginal applicator 232, tampon 202 and inflatable member 234. Tubular applicator or tubular member or means for inserting 232, generally made of plastic material or cardboard, is composed of two tubes generally of cylindrical shape slideable into each other in a telescopic fashion: plunger or actuating means 234 and elongated hollow tube 236 of larger diameter. Elongated hollow tube 236 houses within its lumen tampon 202 and inflatable member 234. Upper end 240 of elongated hollow tube 236 is dome shaped, and, as better shown in FIG. 31A, is formed with stellate opening 242. Resilient triangular concave blades or leaflets curved inward 244 delimit opening 242. Bladder or container or pneumatic source means 67 disclosed in page 9 and illustrated in FIG. 20 is housed within lower segment or chamber 245 of inflatable member 234.

In use the operator inserts dome shaped end 240 of applicator 232 into the vaginal canal lower segment through the vaginal orifice. The operator then pushes plunger 234 upward in order to insert and deliver tampon 202 with inflatable member 234 connected to it into the vaginal canal. Blades or leaflets 244 oppose the advancement and exit of tampon 202 due to their design and structure through stellate opening 242 providing sufficient resistance to advancement of tampon 202 to cause plunger head 234' to rupture membrane 82 of bladder 67, membrane 82 being of less resistant material than wall of bladder 67. As shown in FIG. 20 rupture of membrane 82 allows mixing of acidic solution 90 with effervescent substrate 89 with generation of $CO_2$. $CO_2$ will inflate inflatable member 234 within the vagina.

Inflatable member 234 can house in its lower chamber 245 bladder or capsule or container or source means of inflation 67' disclosed in page 10 and illustrated in FIG. 21. Plunger head 234' will activate the inflating of member 234 by causing the puncture of bladder 67 via perforating puncher 86.

The actuating of source means of gas to inflate inflatable member 234 can be alternatively achieved by rupture of the wall of capsule or container or source means of gas 67' shown in FIG. 21. Capsule 67' which houses compressed gas 110, can be ruptured simply by direct pressure applied upon its thin weak wall by plunger head 234', being bladder 67' interposed between plunger head 234' and the bottom of tampon 202. As for device 230 above described blades or leaflets 244 provide sufficient resistance to advancement of tampon 202 to allow such a rupture.

Figure 32:
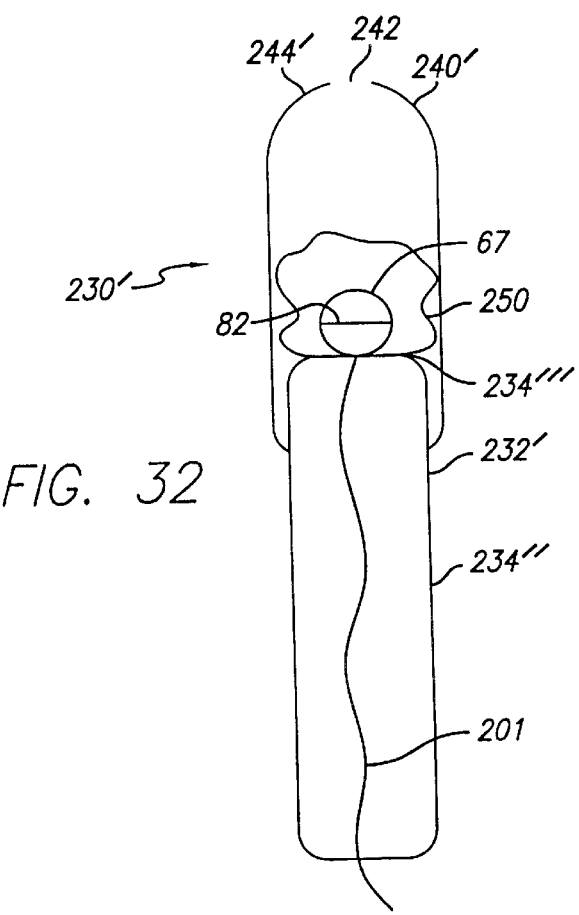
FIG. 32 is a cross section view of a inflatable member housed within an applicator prior to inflation and insertion into the vaginal canal.

FIG. 32 shows device 230' composed of inflatable member 250 contained within applicator 232'. Device 230' is in all similar to device 230 of FIG. 31 with the difference that tampon 202 is no longer present. Inflation of inflatable member 250 is actuated like inflatable member 234 of FIG. 31 except that source means of inflation or gas or bladder 67 is directly pressed against blades 244 of dome shaped end 240' of applicator 232' by plunger head 234" of plunger 234' until rupture of membrane 82 of bladder 67 occurs with subsequent liberation of $CO_2$ to inflate inflatable member 250.

FIGS. 33, 34, 35, 36, 37 and 38 show alternative forms of the catamenial device for blood leakage prevention. In all these embodiment inflation of the balloon or inflatable member occurs by air or gas drawn from the outside into the interior of the balloon and not by air or gas directly originating within the balloon as described for devices illustrated in FIGS. 20, 20A, 21.

More specifically expansion by inflation of balloon occurs by suctioning of air or gas from the outside environment into the interior of the inflatable member or balloon. Suctioning occurs as a result of negative pressure gradient being created within the expandable member or balloon which causes movement of air or gas from the outside into the interior of the expandable member or balloon via an airflow communication between the interior of the balloon and the outside environment.

Figure 33:
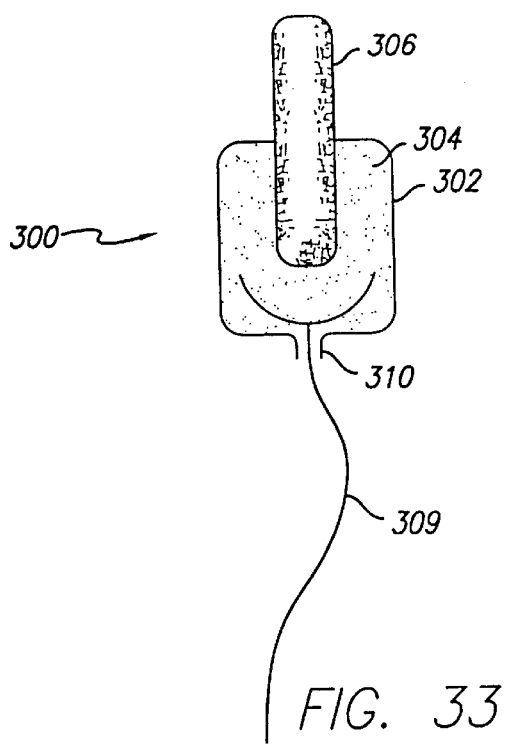
FIG. 33 is a sagittal cross section view of an alternative form of the device combined with a tampon as it appears after inflation.
Figure 34:
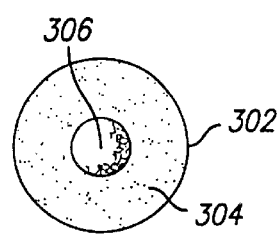
FIG. 34 is a transversal cross section view of the device of FIG. 33.

Device 300, shown in sagittal cross section view in FIG. 33 and in transversal cross section view in FIG. 34, is composed of inflatable member or balloon 302, substantially impermeable to gas and fluids, enveloping inflation member or air suctioning member or open cell foam member 304 and absorbent member or intravaginal tampon 306. Balloon 302 when fully inflated is grossly of cylindrical or conic shape and partially encircles a portion of absorbent member or tampon 306, leaving the rest of tampon 306 exposed for blood absorption. Inflation member 304 can be also of spongiform structure.

Inflatable member or balloon 302 is formed with opening 310 at its base for air flow communication with the outside environment. Suctioning of air into balloon 302, i.e. inflation of balloon 302, occurs by spontaneous distention of open cells foam member 304 housed within balloon 302, from a forced compressed state to a resting distended state. The forced compressed state of open cell foam member 304 can be variously achieved and maintained either by actual mechanical compression of the open cell foam member 304 or by sealing the air flow communication opening 310 between the interior of balloon 302 and the outside environment, once the air or gas is squeezed out or aspirated from the foam. Upon sealing of opening 310, after compression of foam member 304 or aspiration of air from balloon or inflatable member 302, a vacuum pressure will be maintained within inflatable member 302, therefore inflatable member 302 will remain in a contracted state, being inflatable member 302 substantially impermeable to gas beside to fluids. Contraction of inflatable member 302 will facilitate insertion of catamenial device 300 in the vaginal canal.

For the purpose of removal from the vaginal canal device 300 is provided with string 309.

Figure 35:
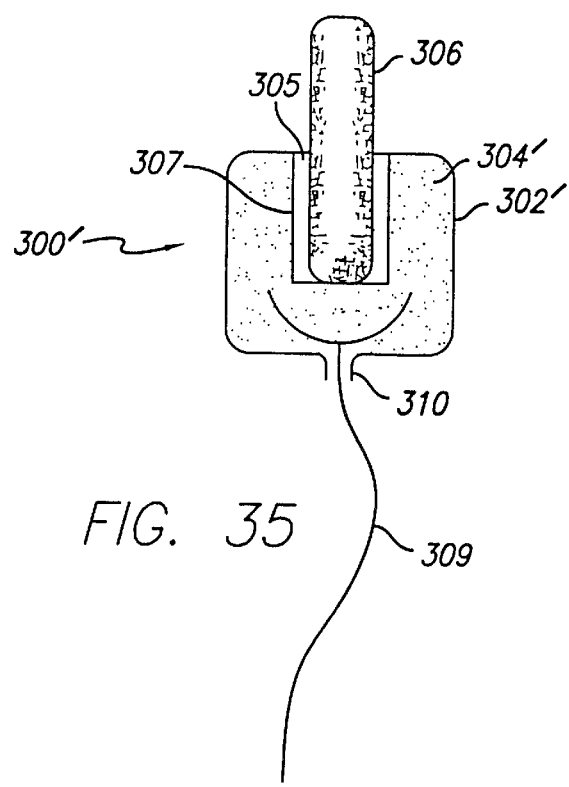
FIG. 35 is a sagittal cross section view of an alternative form of the catamenial device combined with a tampon as it appears after inflation.

FIG. 35 shows an alternative version of the catamenial device, generally indicated at 300', in which balloon 302' is cup shaped upon expansion, being formed with reservoir 305 for blood collection. As in device 300 balloon or inflatable member 302' houses open cell foam member or air suctioning member or inflation member 304' and is formed also with opening or conduit 310. Inflation member 304' can be made of sponge-like material as inflation member 304 of device 300. Lower segment of tampon 306 is housed in reservoir 305, and separated from inner wall 307 of balloon 302'. Device 300' is used as device 300.

Figure 36:
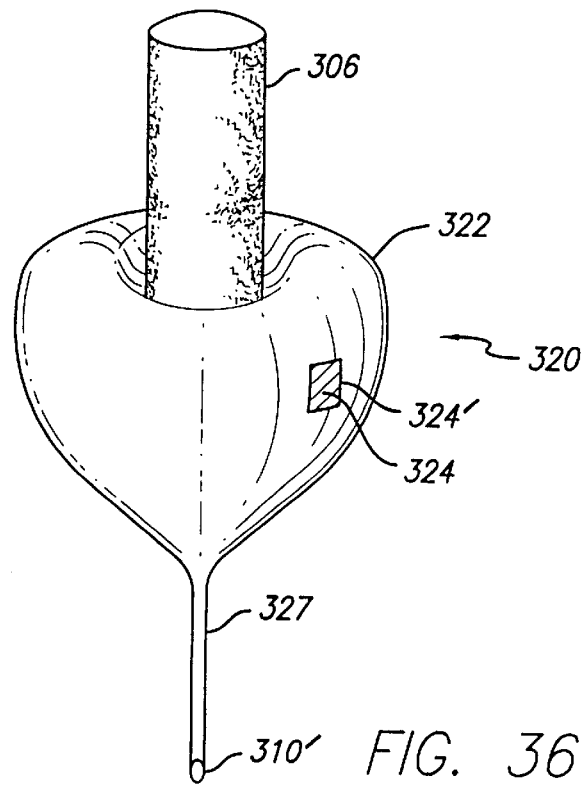
FIG. 36 is a cross section view of an alternative form of the device combined with a tampon as it appears after inflation.

FIG. 36 shows an alternative form of the catamenial device, generally indicated at 320, in which suctioning of air into balloon 322 occurs by spontaneous distension of inflation member 324 which is a resiliently expandable hollow suction bulb member which spontaneously regains its shape after having been compressed if airflow communication is not been closed after compression. Balloon 322 houses suction bulb member 324 visible in FIG. 36 through window 324', created in the drawing for visualization of bulb member 324. Bulb member 324 is provided with conduit 327 having opening 310' for flow communication with the outside environment. Alternatively, suction bulb member 324 may be part of the wall of balloon 322 or fused with it.

Figure 37:
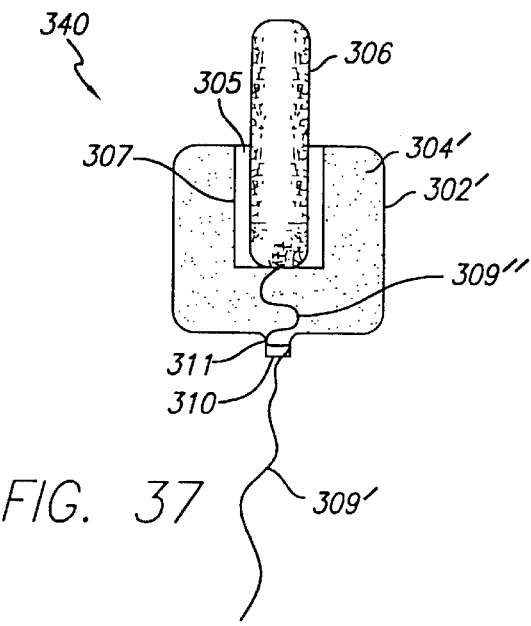
FIG. 37 is a cross section view of a device similar to device of FIG. 36 where the tampon string is connected to the body of the tampon as in a regular tampon.

FIG. 37 shows an alternative form of the catamenial device much similar to device 300' of FIG. 35. In this device, generally indicated at 340, absorbent member or tampon 306 is in fact a regular tampon with string 309' attached to the body of tampon 306. A slack 309" of string 309', is housed within the body of resiliently expandable member 304'. String 309' is attached to balloon 302' via non-airtight attachment 311 in proximity of air conduit or opening 310. Slack 309" facilitates elongation and streaming of balloon or inflatable member 302', which houses foam member 304', upon extraction of device 340 from the vagina by the user pulling on string 309' which in turn will pull attachment 311 causing the above mentioned elongation of inflatable member 302.

Figure 38:
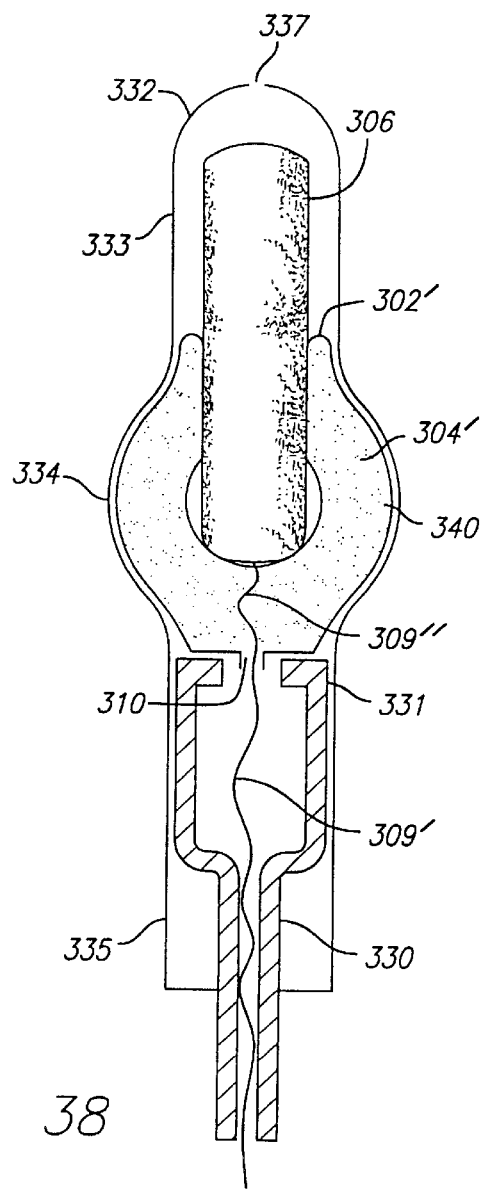
FIG. 38 is a cross sectional view of device of FIG. 37 within an applicator before ejection.

FIG. 38 shows, in cross section, catamenial device 340 of FIG. 37 housed within tampon applicator 332. Applicator 332 may have, as shown in FIG. 38, an enlarged segment, 334, in correspondence of which expandable member 304' may be stored for a long period of time without compromising its full distensibility required after ejection from applicator 332, although some material appears to maintain satisfactory distensibilty after being subjected to high degree of compression for long period of time. Applicator 332 has a distal tubular segment 333 for housing tampon 306 prior to use, and a proximal tubular segment 335 within which applicator plunger 330 is slideably engaged. Applicator plunger 330 is formed with contact head 331.

In use, after insertion of distal tubular segment 333 of applicator 332 into a woman's vagina, plunger 330 is pushed in by the female user to advance catamenial device 340 into the vagina. If expandable member 304' is stored in an enlarged segment of applicator 332, as shown in FIG. 38, expandable member 304', upon forward displacement, will be compressed within segment 333 of applicator 332, with consequent expulsion of air through opening or conduit 310 of inflatable member 302'. Upon exiting of expandable member 304' from applicator 332 through applicator opening 337, expandable member 304' will distend by resiliency creating a negative pressure gradient between the inside of inflatable member 302' and the outside environment causing air to be drawn into inflatable member 302'. In applicators without enlarged segment 334, expandable member 304' will remain housed in a compressed state within a tubular segment such as tubular segment 333 of applicator 332, and will expand upon ejection from the applicator from such compressed state maintained during storage of the device.

Figures 39, 39A:
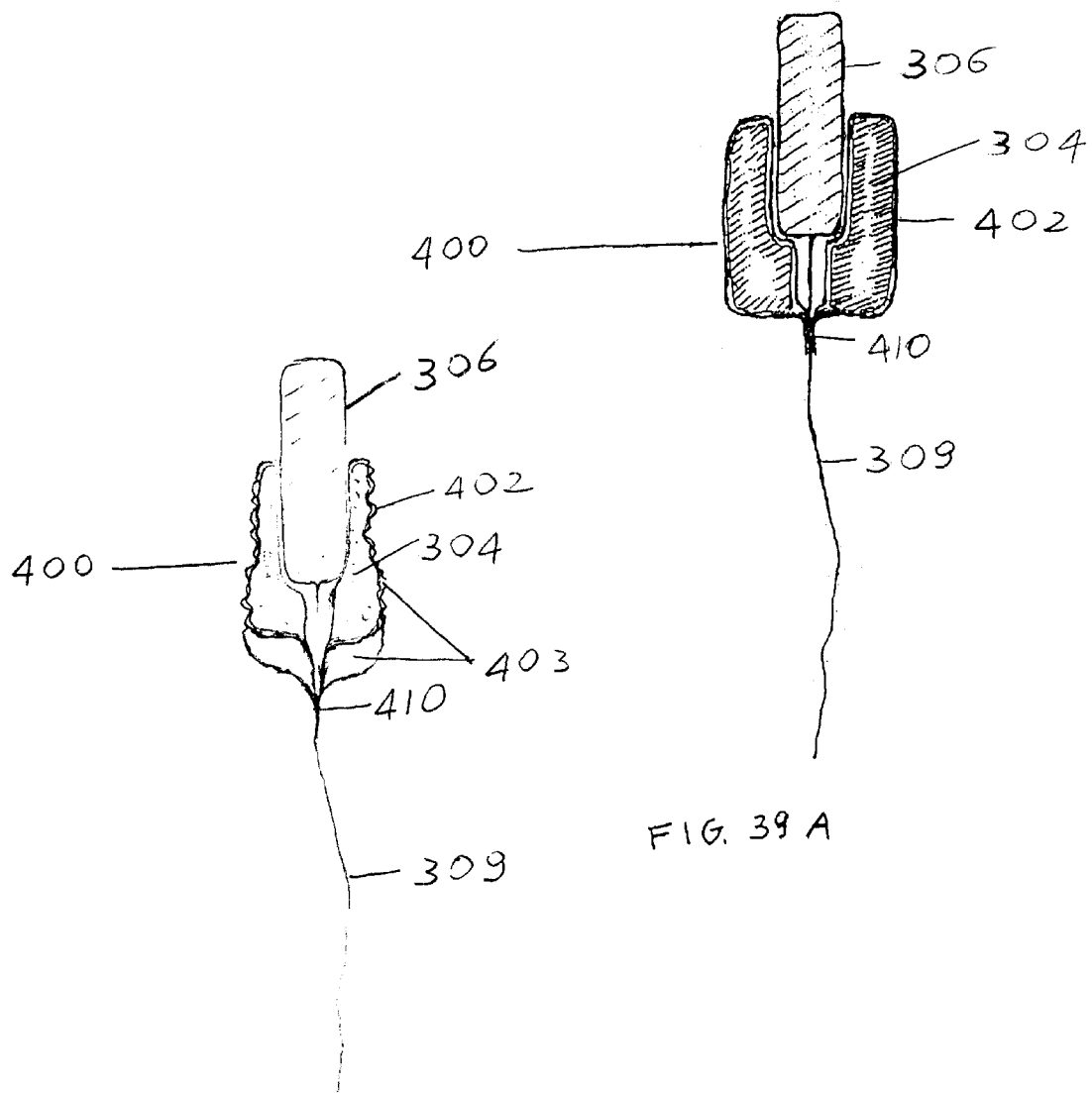
FIG. 39 is a cross section view of an alternative form of the device of FIGS. 33 and 34 combined with a tampon as it appears prior expansion.
FIG. 39A is a cross section view of an alternative form of the device of FIG. 39 as it appears after expansion.

FIGS. 39 and 39A show in cross section an alternative form of catamenial device 300 of FIGS. 33 and 34.

Device 400 of FIG. 39 is similar to device 300 of FIG. 33. However balloon or envelop or inflatable member 402, substantially fluid and gas impermeable, has no communication with the exterior, contrary to balloon 300 of FIGS. 33 and 34, which communicates with the exterior via opening 310. Balloon 402 is sealed around string 309 at inferior pole 410 of balloon 402.

In this version balloon or inflatable member 402 is compliant or elastomeric, made of stretchable material, capable of stretching sufficiently to house a volume of gas or air squeezed out from resilient inflating member or foam member or expandable member 304 prior to insertion into the vaginal canal and inflation of balloon 402. Indeed in device 400 of FIG. 39, prior to insertion into the vaginal canal, foam member 304 is compressed by the user with the fingers or maintained compressed within an applicator. By such compression, the air or gas that is contained within the open cells of the foam prior to compression is squeezed out, therefore displaced, from the foam cells. Since balloon 402 is stretchable, balloon 402 will distend to create space 403 to house the air or gas being displaced from the cells of squeezed foam or inflating member 304. As shown in FIG. 39A, foam member 304, once is no longer compressed or squeezed, regains its expanded pre-compression original state, due to its resiliency and its consequent suctioning, from balloon space 403, of the air or gas that had been housed in such space when the air or gas had been squeezed out of foam member 304, as described above. Expanding by inflation, foam member 304 will inflate balloon 402 for the purpose of sealing the vaginal canal.

FIG. 40 shows a cross section view of an alternative form of the device 300 of FIGS. 33 and 34 much similar to device 400 of FIG. 39. Device 400' of FIG. 40 is in all similar to device 300 of FIGS. 33 and 34, being composed of tampon or absorbent member 306, balloon or inflatable member 402', substantially fluid and gas impermeable, and resilient foam member or inflating member or expandable member 304, except for the difference that balloon or inflatable member 402' of FIG. 40 is made of a non compliant non stretchable material having reservoir 404 of sufficient capacity to house a volume of gas or air squeezed out from inflating member or foam member 304 prior to insertion into the vaginal canal. Indeed as shown in FIG. 40, prior to insertion into the vaginal canal, foam member 304 is compressed by the user with the fingers or maintained compressed within an applicator as shown in FIG. 41. By such compression, the air or gas that is contained within the open cells of the foam prior to compression is squeezed out, therefore displaced, from the foam cells of foam member 304 into balloon reservoir 404. Balloon reservoir 404 is sufficiently large to house the air or gas squeezed out from foam member or inflating member 402'. As shown in FIG. 40A, foam member 304, once is no longer compressed or squeezed, will regain its expanded original pre-compression state, due to its resiliency and its consequent suctioning, from balloon reservoir 404, of the air or gas that had been housed in such space when the air or gas had been squeezed out of foam member 304, as described above. Expanding by inflation, foam member 304 will inflate balloon 402' for the purpose of sealing the vaginal canal.

FIG. 41 shows device 400' within applicator 420 ready to be deployed into the vaginal canal. Applicator 420 is composed of two tubes generally of cylindrical shape slideable into each other in a telescopic fashion: plunger or actuating means 422 and elongated hollow tube 424 of larger diameter. Both can be made of cardborad or plastic and have sufficiently rigid walls. Elongated hollow tube 424 houses within its lumen device 400' composed of tampon 306, balloon 402' with reservoir 404 and inflating member or foam member 304. Upper end 426 of elongated hollow tube 424 is generally dome shaped and is formed with opening 428.

In use, device 400' is ejected out from applicator 420 by the user acting on plunger 422. Once device 400' is out of applicator 420, foam member 304 no longer maintained compressed or squeezed by the relatively rigid walls 423 of elongated hollow tube 424, will regain its expanded original pre-compression state, due to its resiliency and its consequent suctioning, from balloon reservoir 404, of the air or gas that had been housed in such space when the air or gas had been squeezed out of foam member 304, as described above. Expanding by inflation, foam member 304 will inflate balloon 402' for the purpose of sealing the vaginal canal.

Device 400 of FIGS. 39 and 39A can also be used within applicator 420 as device 400' of FIGS. 40 and 40A with the same modalities.

What we claim is:

1. A catamenial device comprising:
   a blood absorbing member,
   an expandable member connected to said blood absorbing member,
   a substantially fluid-impermeable envelop enveloping said expandable member in its entirety, said envelop, upon compression of said expandable member, allowing transfer of gas or fluids content of the expandable member out of said expandable member into an area within the confinement of said envelop, and, upon expansion of said expandable member, allowing transfer of said gas or fluids contained within said area into said expandable member.

2. The device of claim 1 wherein the area within the confinement of said envelop is a reservoir for gas or air.

3. The device of claim 1 wherein said envelop is made of stretchable material.

4. The device of claim 1 wherein said envelop is made of resilient material.

5. The device of claim 1 wherein said envelop is made of non compliant material.

6. The device of claim 1 wherein said envelop assumes a cup-shaped form when expanded.

7. A catamenial device comprising:
   a blood absorbing member,
   an expandable member connected to said blood absorbing member,
   a substantially fluid-impermeable balloon enveloping said expandable member in its entirety, said balloon having a reservoir of sufficient capacity to receive gas or air squeezed out from said expandable member upon compression of said expandable member.

8. A catamenial device for insertion into a vaginal canal having a wall, comprising:
   a blood absorbing member exposed for blood absorption;
   an inflatable member to seal the vaginal canal upon inflation, said inflatable member comprising an airflow communication between an interior and outside of said inflatable member;
   and an inflation member housed within said inflatable member to inflate said inflatable member, wherein said inflation member is a resiliently expandable member to expand said inflatable member to create a negative pressure gradient between air pressure inside said inflatable member and air pressure outside said inflatable member and,
   consequently, via said airflow communication, creating an airflow into said inflatable member to inflate said inflatable member, and wherein said inflatable member assumes a cup shaped form when expanded.

* * * * *